US007684864B2

(12) United States Patent
Olson et al.

(10) Patent No.: US 7,684,864 B2
(45) Date of Patent: Mar. 23, 2010

(54) SUBCUTANEOUS CARDIOVERTER-DEFIBRILLATOR

(75) Inventors: Walter H. Olson, North Oaks, MN (US); King Y. Moy, Tinley Park, IL (US); Joey G. Nakayama, Chicago, IL (US); Gary F. Prokop, Wheaton, IL (US); Gary J. Stilwell, Chicago, IL (US)

(73) Assignee: Medtronic, Inc., Minneapolis, MN (US)

( * ) Notice: Subject to any disclaimer, the term of this patent is extended or adjusted under 35 U.S.C. 154(b) by 344 days.

(21) Appl. No.: 11/116,577

(22) Filed: Apr. 28, 2005

(65) Prior Publication Data

US 2006/0247688 A1    Nov. 2, 2006

(51) Int. Cl.
*A61N 1/02* (2006.01)

(52) U.S. Cl. ............................................ 607/36; 607/5

(58) Field of Classification Search .................... 607/5, 607/36
See application file for complete search history.

(56) References Cited

U.S. PATENT DOCUMENTS

| 5,331,966 | A | * | 7/1994 | Bennett et al. ............... 600/508 |
| 5,554,194 | A |   | 9/1996 | Sanders |
| 5,645,586 | A | * | 7/1997 | Meltzer .................... 623/11.11 |
| 5,683,431 | A | * | 11/1997 | Wang .......................... 607/28 |
| 6,269,266 | B1 |   | 7/2001 | Leysieffer |
| 6,358,281 | B1 |   | 3/2002 | Berrang et al. |
| 6,445,956 | B1 | * | 9/2002 | Laird et al. .................... 607/61 |
| 6,675,042 | B2 | * | 1/2004 | Swerdlow et al. ............... 607/8 |
| 7,054,691 | B1 |   | 5/2006 | Kuzma et al. |
| 7,120,495 | B2 | * | 10/2006 | Bardy et al. ................... 607/36 |
| 7,212,864 | B2 | * | 5/2007 | Wahlstrand et al. ........... 607/36 |
| 7,263,401 | B2 |   | 8/2007 | Scott et al. |
| 7,363,082 | B2 |   | 4/2008 | Ransbury et al. |
| 7,392,089 | B2 |   | 6/2008 | Wahlstrand et al. |
| 7,529,586 | B2 | * | 5/2009 | Wahlstrand et al. ........... 607/36 |
| 7,529,589 | B2 |   | 5/2009 | Williams et al. |
| 2001/0011185 | A1 |   | 8/2001 | Dobak, III et al. |
| 2002/0068958 | A1 |   | 6/2002 | Bardy et al. |
| 2002/0107547 | A1 | * | 8/2002 | Erlinger et al. ................. 607/5 |
| 2004/0249431 | A1 |   | 12/2004 | Ransbury et al. |
| 2005/0043765 | A1 |   | 2/2005 | Williams et al. |
| 2008/0167702 | A1 |   | 7/2008 | Ransbury et al. |
| 2009/0036939 | A1 |   | 2/2009 | Singh et al. |

FOREIGN PATENT DOCUMENTS

| WO | WO 03089059 | 10/2003 |
| WO | 2004052455 | 6/2004 |

\* cited by examiner

*Primary Examiner*—Carl H Layno
*Assistant Examiner*—Brian T Gedeon
(74) *Attorney, Agent, or Firm*—Stephen W. Bauer; Michael C. Soldner

(57) ABSTRACT

SubQ ICDs are disclosed that are entirely implantable subcutaneously with minimal surgical intrusion into the body of the patient and provide distributed cardioversion-defibrillation sense and stimulation electrodes for delivery of cardioversion-defibrillation shock and pacing therapies across the heart when necessary. Configurations include one hermetically sealed housing with 1 or, optionally, 2 subcutaneous sensing and cardioversion-defibrillation therapy delivery leads or alternatively, 2 hermetically sealed housings interconnected by a power/signal cable. The housings are generally dynamically configurable to adjust to varying rib structure and associated articulation of the thoracic cavity and muscles. Further the housings may optionally be flexibly adjusted for ease of implant and patient comfort.

15 Claims, 26 Drawing Sheets

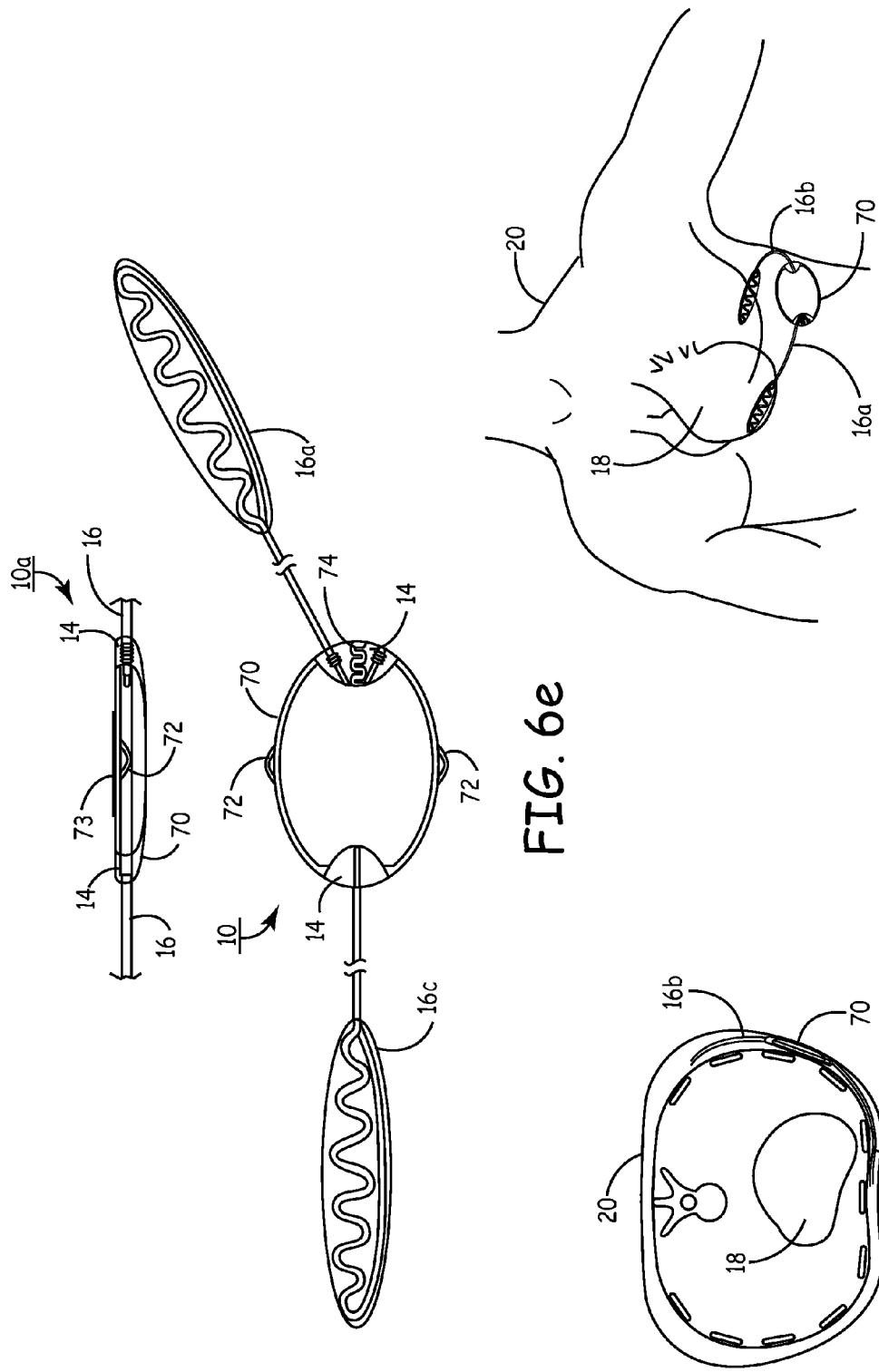

SUBCUTANEOUS CARDIOVERTER-DEFIBRILLATOR

FIELD OF THE INVENTION

The present invention generally relates to implantable medical devices, particularly implantable cardioverter-defibrillators that are entirely implanted subcutaneously (SubQ ICD) and, more particularly, have no leads or electrodes contacting the heart or extending into the thoracic cavity.

BACKGROUND OF THE INVENTION

Many types of implantable medical devices (IMDs) have been clinically implanted over the last twenty years that deliver relatively high-energy cardioversion and/or defibrillation shocks to a patient's heart when a malignant tachyarrhythmia, e.g., atrial or ventricular fibrillation, is detected. Cardioversion shocks are typically delivered in synchrony with a detected R-wave when fibrillation detection criteria are met, whereas defibrillation shocks are typically delivered when fibrillation criteria are met and an R-wave cannot be discerned from the EGM.

The current state of the art of ICDs or implantable pacemaker/cardioverter/defibrillators (PCDs) includes a full featured set of extensive programmable parameters which includes multiple arrhythmia detection criteria, multiple therapy prescriptions (for example, stimulation for pacing in the atrial, ventricular and dual chamber; atrial and ventricular for bradycardia; bi-atrial and/or bi-ventricular for heart failure; and arrhythmia overdrive or entrainment stimulation) and high level stimulation for cardioversion and/or defibrillation, extensive diagnostic capabilities and high speed telemetry systems. These full-featured ICDs or PCDs, hereinafter IMD, are typically implanted into patients who have had, and survived, a significant cardiac event (such as sudden death). Additionally, these devices are expected to last up to 5-8 years and/or provide at least 200 life saving therapy shocks.

Even though there have been great strides in size reduction over the past 20 years, the incorporation of all these features in an IMD, including the longevity requirements, dictates that the devices be typically much larger than current state of the art pacemakers. Such devices are often difficult to implant in some patients (particularly children and thin, elderly patients) and typically require the sacrifice of 1 or 2 veins to implant the lead system because leads associated with the implantation of an IMD utilize a transvenous approach for cardiac electrodes and lead wires. The defibrillator canister/housing is generally implanted as an active can for defibrillation and electrodes positioned in the heart are used for pacing, sensing and detection of arrhythmias.

Although IMDs and implant procedures are very expensive, most patients who are implanted have experienced and survived a sudden cardiac death episode because of interventional therapies delivered by the IMDs. Survivors of sudden cardiac death episodes are in the minority, and studies are ongoing to identify patients who are asymptomatic by conventional measures but are nevertheless at risk of a future sudden death episode. Current studies of patient populations, e.g., the MADIT II and SubQ ICD HeFT studies, are establishing that there are large numbers of patients in any given population that are susceptible to sudden cardiac death, that they can be identified with some degree of certainty and that they are candidates for a prophylactic implantation of a defibrillator (often called primary prevention). However, implanting currently available IMDs in all such patients would be prohibitively expensive. Further, even if the cost factor is eliminated there is shortage of trained personnel and implanting resources.

One option proposed for this patient population is to implant a prophylactic subcutaneous implantable cardioverter/defibrillator (SubQ ICD) such that when these patients receive a shock and survive a cardiac episode, they will ultimately have an implant with a full-featured ICD and transvenous leads.

While there are a few small populations in whom SubQ ICD might be the first choice of implantation for a defibrillator, the vast majority of patients are physically suited to be implanted with either an ICD or SubQ ICD. It is likely that pricing of the SubQ ICD will be at a lower price point than an ICD. Further, as SubQ ICD technology evolves, it may develop a clear and distinct advantage over ICDs. For example, the SubQ ICD does not require leads to be placed in the bloodstream. Accordingly, complications arising from leads placed in the cardiovasculature environment is eliminated. Further, endocardial lead placement is not possible with patients who have a mechanical heart valve implant and is not generally recommended for pediatric cardiac patients. For these and other reasons, a SubQ ICD may be preferred over an ICD.

Therefore, for these and other reasons, a need exists for a simplified, cosmetically and ergonomically adaptive SubQ ICD that can be implanted beneath the skin and over the ribcage. Specifically, the SubQ ICD should be implantable with minimal trauma in a wide range of patients by surgeons employing conventional surgical instruments and monitoring equipment so as to make the implantation process less expensive and more widely available.

The present invention describes several SubQ ICD configurations adapted for subcutaneous implant. The SubQ ICD's of the present invention would be capable of delivering a limited number of shocks at maximal shock energy with an additional capability to provide pacing therapy for temporary post shock cardiac support or bradycardia pacing.

SUMMARY OF THE INVENTION

Apparatuses and methods are disclosed relating to various types of SubQ ICD's with geometries, shapes and sizes adapted for subcutaneous implant. In a prophylactic application, for example, some embodiments form SubQ ICD systems that can be placed completely in the subcutaneous or submuscular position without the need to place leads or electrodes in the vasculature of the patient. One set of embodiments of the invention provides a variety of configurations for delivering cardioversion/defibrillation therapy with a vector of energy controlled by operative circuitry of a non-active-can type SubQ ICD. In one form of the invention, the SubQ ICD housing can be conveniently implanted in a surgically-created subcutaneous or submuscular pocket formed over or near a portion of the cardiac notch, or sternum of a patient and adjacent a portion of pectoralis major.

In yet another embodiment, the SubQ ICD may be implanted in a pocket formed adjacent a portion of the external abdominal oblique. In another embodiment, the SubQ ICD housing may be implanted in a pocket formed adjacent a portion of the serratus anterior.

In one embodiment, the SubQ ICD electrically couples to one or more elongated, coil-type high voltage electrodes with the electrodes disposed in a location providing defibrillation vectors covering adequate mass of myocardial tissue to achieve defibrillation and deliver pacing therapy. Specifically, leads may be substantially implanted adjacent a portion of the external abdominal oblique; adjacent the cardiac notch; adjacent a portion of the serratus anterior; and adjacent a portion of the latissimus dorsi.

In one embodiment, more than one high voltage electrodes are implemented with the SubQ ICD connected to all electrodes. The one or more high voltage electrodes may include a set of coil electrodes disposed in an orientation relative to a patient's heart that provides several different therapy delivery vectors therebetween.

BRIEF DESCRIPTION OF THE DRAWINGS

These and other features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 6E illustrates a multi-planar view of an alternate arrangement SubQ ICD of the sixth embodiment according to the present invention;

FIGS. 6F and 6G illustrate a cross-sectional view of the thoracic cavity and the deployment of the SubQ ICD and the SubQ ICD of the sixth embodiment implanted in a patient, respectively;

DETAILED DESCRIPTION OF THE INVENTION

Figure 1A:
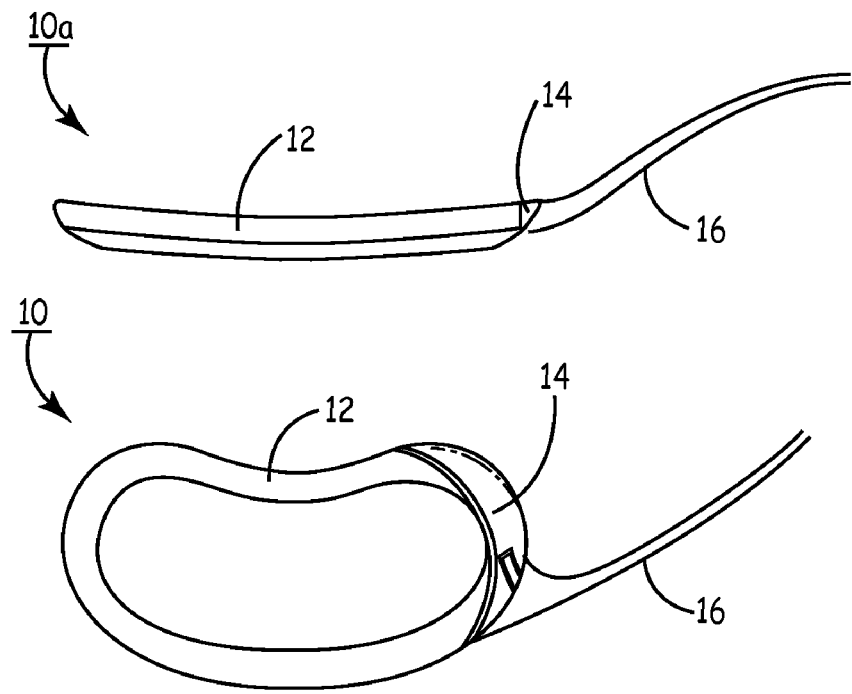
FIG. 1A depicts a multi-planar view of a SubQ ICD of a first embodiment of the present invention.

FIG. 1A depicts a multi-planar view of a first embodiment of the present invention. SubQ ICD 12 is an ovoid, substantially, kidney-shaped housing with connector 14 for attaching a subcutaneous sensing and cardioversion/defibrillation therapy delivery lead 16. SubQ ICD 12 may be constructed of stainless steel, titanium or ceramic as described in U.S. Pat. Nos. 4,180,078 "Lead Connector for a Body Implantable Stimulator" to Anderson and 5,470,345 "Implantable Medical Device with Multi-layered Ceramic Enclosure" to Hassler, et al. The electronics circuitry of SubQ ICD 10 (described herein pertaining to FIG. 21) may be incorporated on a polyamide flex circuit, printed circuit board (PCB) or ceramic substrate with integrated circuits packaged in leadless chip carriers and/or chip scale packaging (CSP). In one of the views, the concave construction of SubQ ICD 12 is illustrated. The minor concavity of the housing of SubQ ICD 12 follows the natural curve of the patient's median ribcage at about the cardiac notch. The central curved depression shown in frontal elevation view 10 is ergonomically aligned to minimize patient discomfort when seated, bending over and/or during normal torso movement.

SubQ ICD 12 is shown coupled to subcutaneous lead 16. At connector block 14, the crescent-shaped connector block 14 enables a reliable curvilinear connection between lead 16 and the curved edge of SubQ ICD 12. Lead 16, like the other leads discussed below, includes an elongated lead body carrying conventional, mutually insulated conductors, each coupled to an electrode.

Figure 1B:
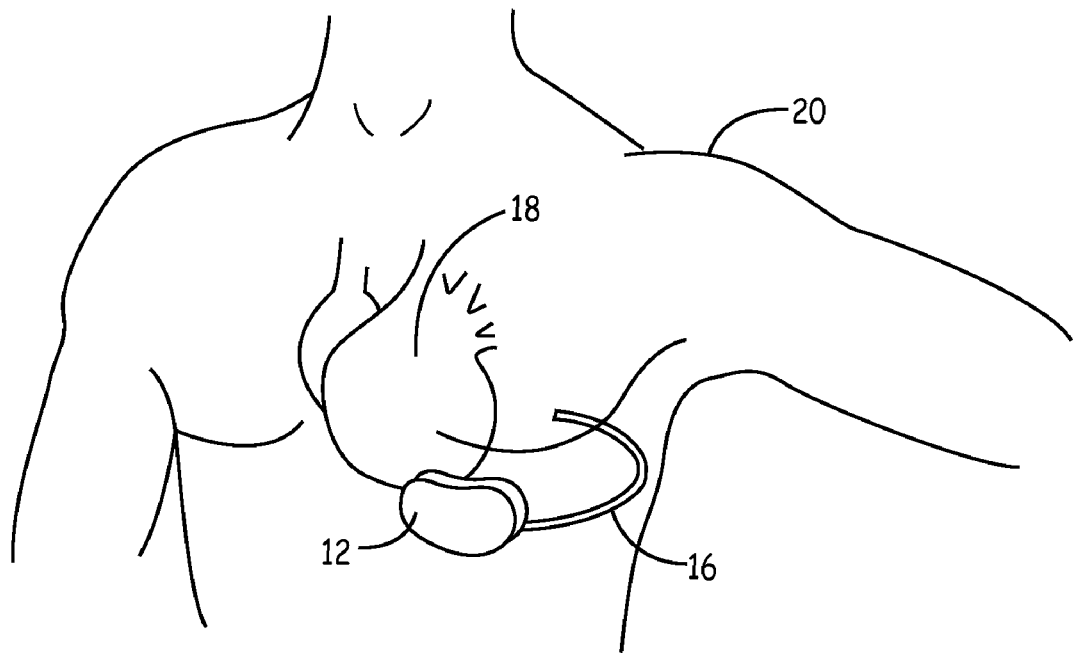
FIG. 1B illustrates a SubQ ICD of the first embodiment implanted in a patient.

FIG. 1B illustrates SubQ ICD 12 implanted in patient 20. Specifically, lead 16 is advanced adjacent the cardiac notch and tunneled subcutaneously from the median implant pocket of SubQ ICD 12 laterally and posteriorly to the patient's back to a location opposite the heart such that the heart 18 is disposed between the SubQ ICD 12 and the distal end of subcutaneous lead 16. The implant location of SubQ ICD 12 and lead 16 is typically subcutaneously above the external abdominal oblique. The distal end of lead 16 is tunneled above the external oblique muscle extending over to a portion of the latissimus dorsi.

Figure 2A:
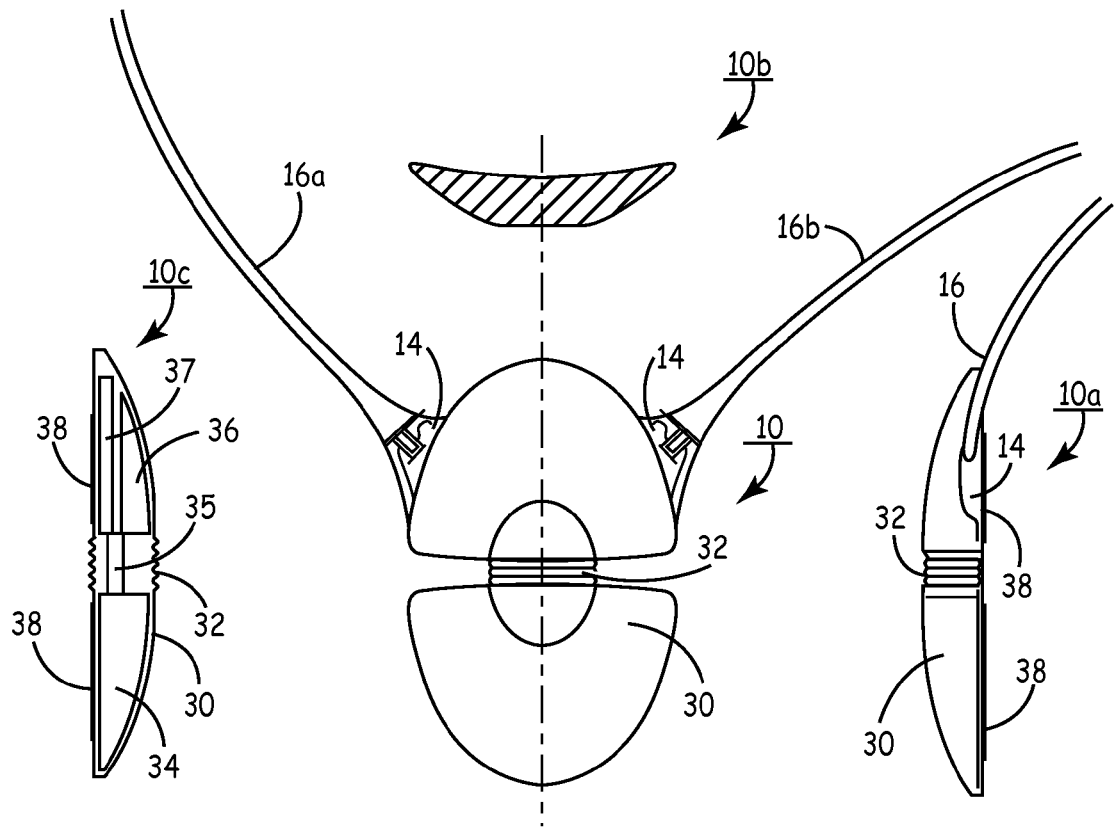
FIG. 2A illustrates a multi-planar view of a SubQ ICD of a second embodiment of the present invention.

FIG. 2A is a multi-planar view of SubQ ICD 30, a second embodiment of the present invention. SubQ ICD 30 is a convex, flexible ovaloid-shaped housing with connectors 14 (2 shown) for attaching 2 subcutaneous sensing and cardioversion/defibrillation therapy delivery leads 16A and 16b. SubQ ICD 30 may be constructed of stainless steel, titanium or ceramic. View 10A is a side view of SubQ ICD 30 showing the tapered housing 30, a mid-line flexible joint 32, connector 14, lead 16 and active can electrode 38. The active can electrode 38 allows sensing and cardioversion, defibrillation and/or pacing therapy delivery between the SubQ ICD 30 and one or both leads 16A or 16b. The jointed housing 30 allows physician flexibility in selecting implant locations and accommodates variances in size and weight of patients for implant. Additionally, the flexible housing provides less patient discomfort in sitting, bending over and/or during normal torso movement because the configurations allows dynamic adjustment to the patient's dynamic and muscular movements. View 10b is a top cut-away view of the SubQ ICD 30 showing the convex construction that promotes ease of subcutaneous implant by following the natural curve of the patient's lateral ribcage. View 10c is a vertical cross section of SubQ ICD 30 showing internal components that will be described in more detail hereinbelow. Shown in this view are battery 36, electronics module 37, high voltage capacitors 34, flex circuit 35 and flexible housing joint 32.

Figure 2B:
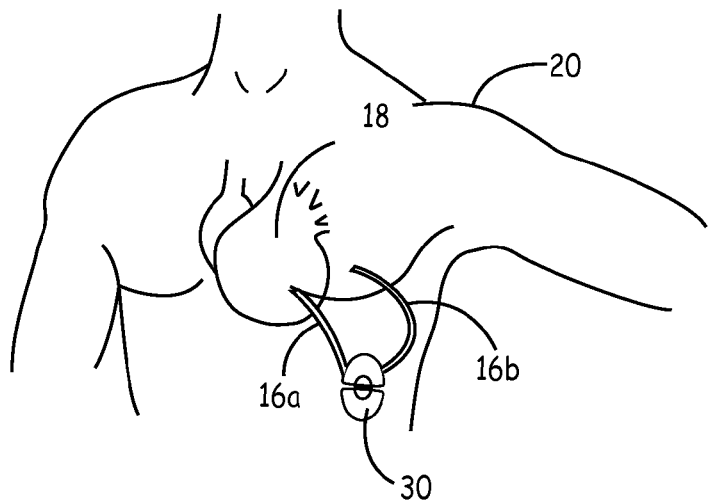
FIG. 2B illustrates a SubQ ICD of the second embodiment implanted in a patient.

FIG. 2B illustrates implant position of SubQ ICD 30 and leads 16A and 16B according to a second embodiment of the invention. SubQ ICD 30 is implanted subcutaneously over a portion of the external oblique muscle laterally outside the $20^{th}$ ribcage of patient 20. Lead 16A is tunneled subcutaneously from the lateral implant pocket of SubQ ICD 30 anterially and medially to the cardiac notch. Further, lead 16b is tunneled posterially adjacent the latissimus dorsi, to the patient's back to a location opposite the heart such that the heart 18 is disposed between the distal end of subcutaneous lead 16A and the distal end of subcutaneous lead 16b.

Figure 3A:
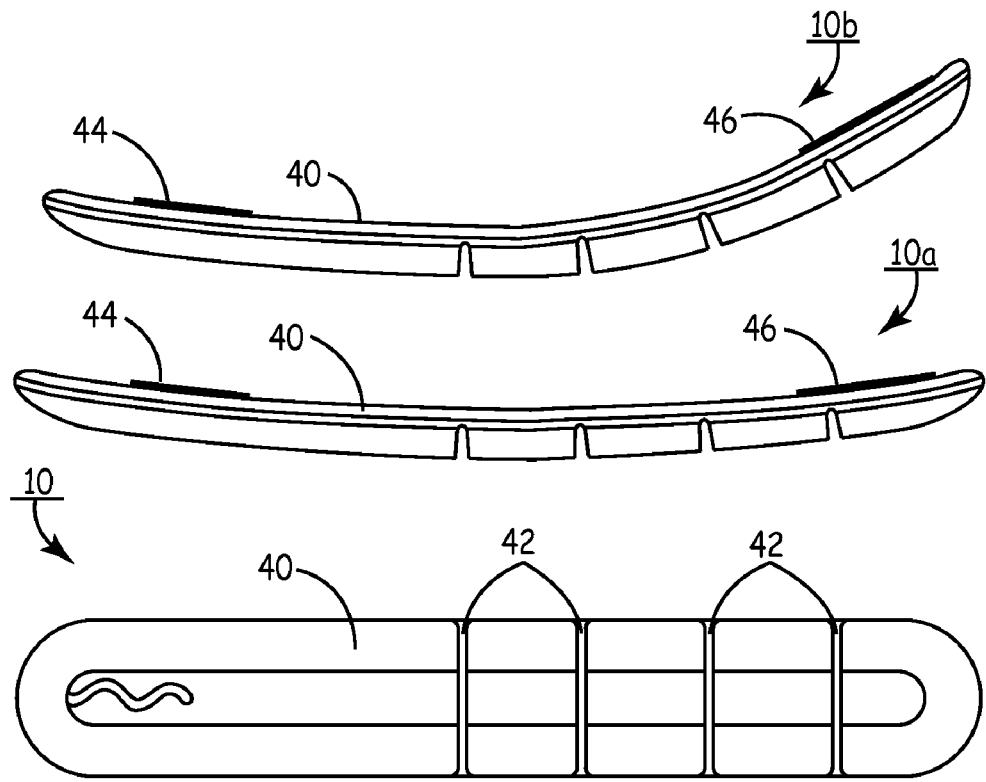
FIG. 3A illustrates a multi-planar view of a third embodiment of a SubQ ICD in accordance with the present invention.
Figure 3B:
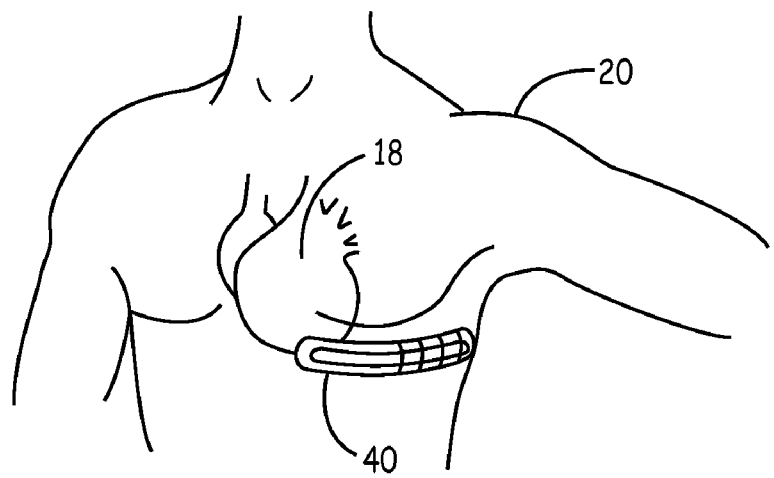
FIG. 3B illustrates the SubQ ICD of the third embodiment implanted in a patient.

FIG. 3A is a multi-planar view of a third embodiment of SubQ ICD 40. SubQ ICD 40 is an elongated slender ellipsoid with sections of partially articulating dynamic segments having surface mounted subcutaneous sensing and cardioversion/defibrillation therapy delivery electrodes 44 and 46. SubQ ICD 40 may be constructed of stainless steel, titanium or ceramic or equivalent. View 10A is a top view of SubQ ICD 40 showing the segmented construction. Electrodes 44 and 46 located at opposite ends of SubQ ICD 40 are typically 100 $mm^2$ to 1000 $mm^2$. View 10b is a further top view showing the dynamic flexibility of SubQ ICD 40 in which it assumes a dynamically adjustable, compressive and tensile opposing surfaces when implanted outside the thoracic cavity over the ribs. Specifically, in its normal position, SubQ ICD 40 is substantially flat both at the top and bottom surfaces. However, when implanted, SubQ ICD 40 dynamically forms a concave and convex surface at the flat top and segmented bottom surfaces when tunneled into the subcutaneous regions of the thoracic cavity above the ribs or the intercostals region therebetween. As illustrated in FIG. 3B, SubQ ICD 40 dynamically adjusts to wrap around the ribcage with electrode 44 anterior to the cardiac notch and the SubQ ICD 40 is positioned such that electrode 46 is laterally located in opposition to electrode 46 thereby positioning heart 18 between the electrodes. The dynamic configurability of SubQ ICD 40 creates an external surface that is convex and slightly bent in two directions and at the same time twisted on its long axis to closely fit over the ribs.

Figure 4A:
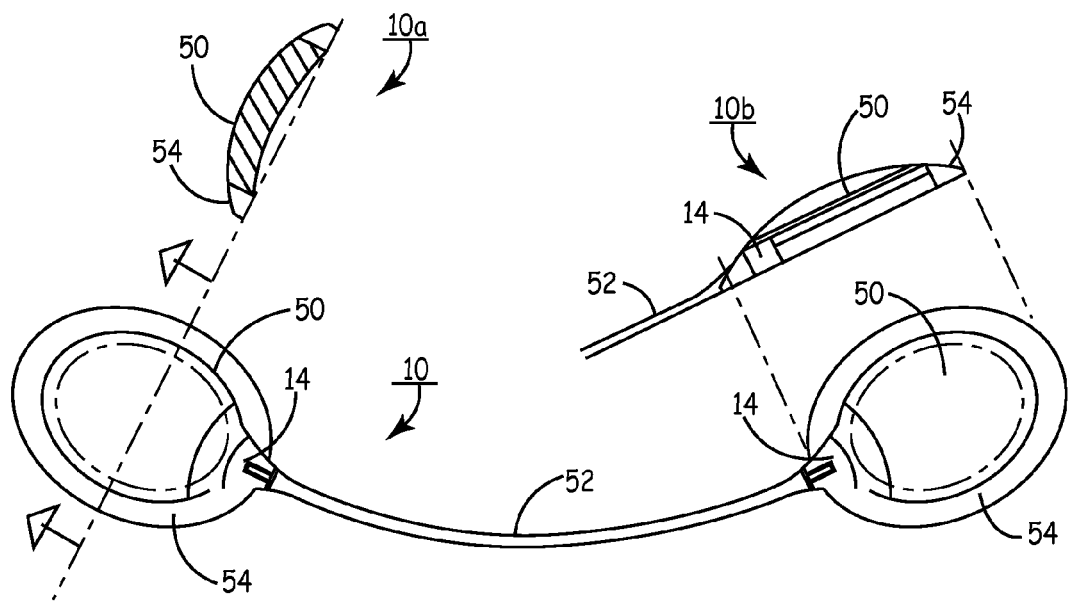
FIG. 4A illustrates the SubQ ICD of the fourth embodiment in accordance with the present invention.

FIG. 4A is an illustration of the fourth embodiment of the present invention. SubQ ICD 50 housings are connected by an interconnecting lead 52 containing power, control, sensing and therapy delivery conductors. The SubQ ICD 50 contains integrated subcutaneous sensing and cardioversion/defibrillation therapy delivery electrodes. SubQ ICD 50 may be constructed of stainless steel, titanium or ceramic. View 10A is a cross sectional view through one of the SubQ ICD 50 housings showing the concave inner surface to enable unobtrusive subcutaneous implant because the oval profile of SubQ ICD 50 is designed to follow the natural curve of the patient's median cardiac notch and posterior ribcage. Integrated electrodes (not shown) located on the inner surfaces of SubQ ICD 50 are typically 100 $mm^2$ to 1000 $mm^2$ in active area. View 10b is a top view of SubQ ICD 50 showing a convex domed top and a substantially flat bottom.

Figure 4B:
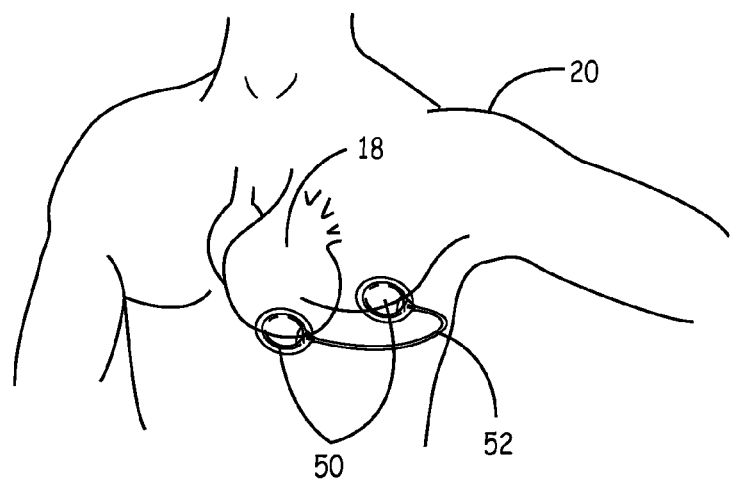
FIG. 4B illustrates the SubQ ICD of the fourth embodiment implanted in a patient.

FIG. 4B illustrates SubQ ICD 50 implanted in patient 20. Specifically, SubQ ICD 50 is implanted outside the ribcage with a first SubQ ICD 50 housing anterior to the cardiac notch and the other SubQ ICD 50 housing tunneled and positioned posteriorly in relation to heart 18.

Figure 4C:
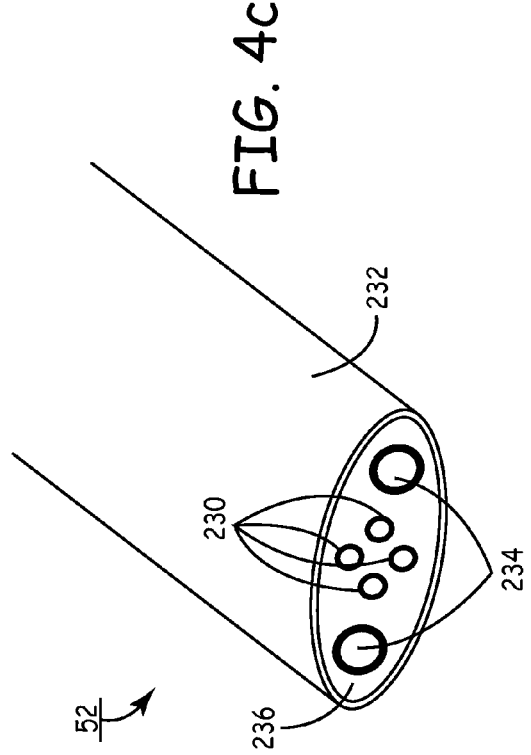
FIG. 4C illustrates a cross-sectional view of a cable connecting the two SubQ ICD's of the fourth embodiment in accordance with the present invention.

FIG. 4C illustrates a cross-sectional view of the interconnecting cable 52. The outer sheath of cable 52 consists of a urethane or equivalent sheath 232 with an inner insulation 236 of HP Silicone. The power, control and sensing conductors 230 are wrapped with ETFE while the defibrillation conductors 234 are constructed of Ag/MP35N and wrapped with ETFE and reinforced with tensile material.

Figure 4F:
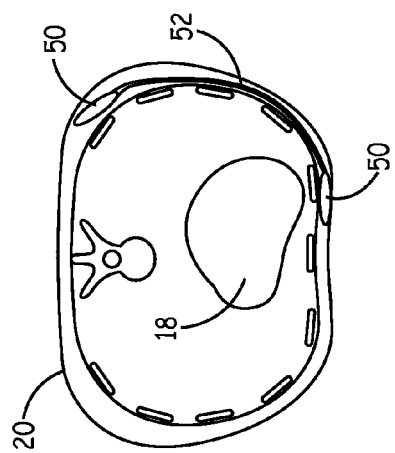
FIGS. 4D, 4E and 4F illustrate a cross-sectional view of a patient taken through the thoracic cavity and center of the heart showing the deployment and arrangement of the fourth embodiment SubQ ICD in accordance with the present invention.
Figure 4E:
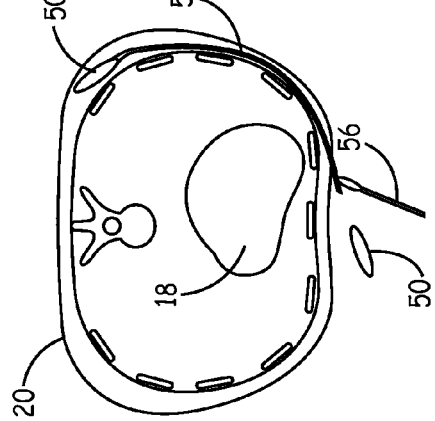
Figure 4D:
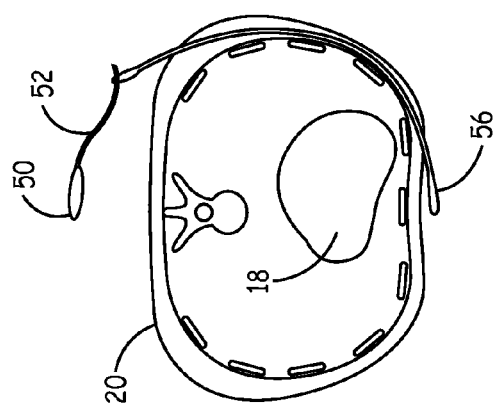

FIGS. 4D, 4E and 4F illustrate cross-sectional views taken through the thoracic cavity and center of the heart showing the deployment and implant of SubQ ICD 50. FIG. 4D shows a tunneling tool 56 entering the patient's body 20 at a first incision anterior to the cardiac notch, tunneled laterally and posteriorly to exit at a second incision in the patient's back adjacent a portion of the latissimus dorsi. The SubQ ICD 50 and interconnecting cable 52 are attached to the tunneling tool 56, which is retracted, and the SubQ ICD 50 and cable 52 are pulled into a posterior implant location as shown in FIG. 4E. The second housing of SubQ ICD 50 is attached to the interconnecting cable 52 and placed into an implant pocket anterior to the cardiac notch as shown in FIG. 4F.

Figure 5A:
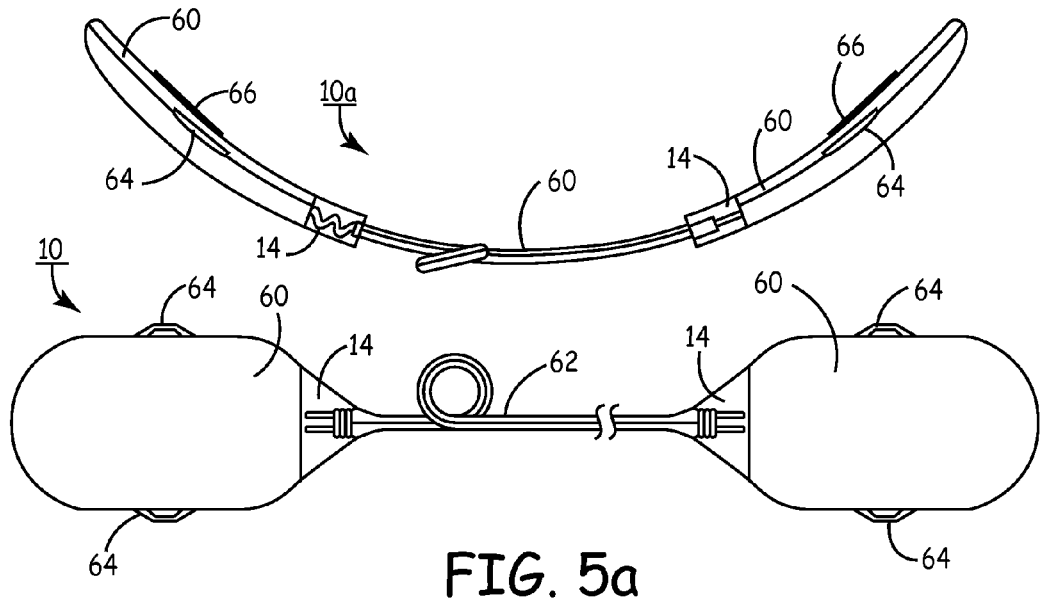
FIG. 5A illustrates a multi-planar view of a SubQ ICD in accordance with a fifth embodiment of the present invention.

FIG. 5A illustrates a fifth embodiment of the present invention. SubQ ICD 50 consists of two rounded beetle-shaped housings connected by an interconnecting lead 62. The SubQ ICD 60 may be constructed of stainless steel, titanium or ceramic. Excess length and a strain relief loop are provided in cable 62. The SubQ ICD 60 contains integrated subcutaneous sensing and cardioversion/defibrillation therapy delivery electrodes 66. Suture loops 64 are provided on each housing to enable the fixation of each housing in a predetermined location for proper stimulation and to prevent device migration. As is shown in the top view, SubQ ICD 60 housing includes a concave inner surface to enable a compliant subcutaneous movement by the canisters following the natural curve of the patient's median cardiac notch and posterior ribcage. Integrated electrodes 66 located on the inner surfaces of canisters 60 are typically 100 mm$^2$ to 1000 mm$^2$ in active area.

Figure 5B:
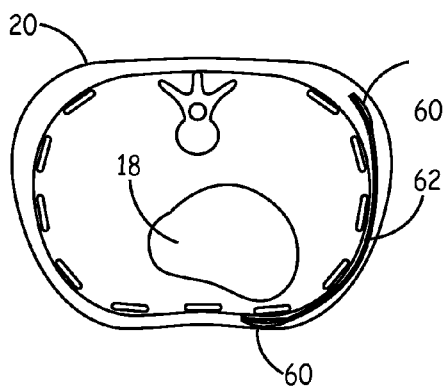
FIGS. 5B and 5C illustrate a cross-sectional view of a patient taken through the thoracic cavity and center of the heart with the deployment and arrangement of the SubQ ICD, and the SubQ ICD of the fifth embodiment implanted in a patient, respectively.

FIG. 5B illustrates a cross-sectional view through the thoracic cavity and the center of the heart 18 showing the implant location for SubQ ICD 60. Specifically, a first housing of SubQ ICD 60 is implanted anterior to the cardiac notch and a second housing of SubQ ICD 60 located posteriorly. Interconnecting cable 62 containing power, control, sensing and therapy delivery conductors is located between the SubQ ICD 60 housing as shown.

Figure 5C:
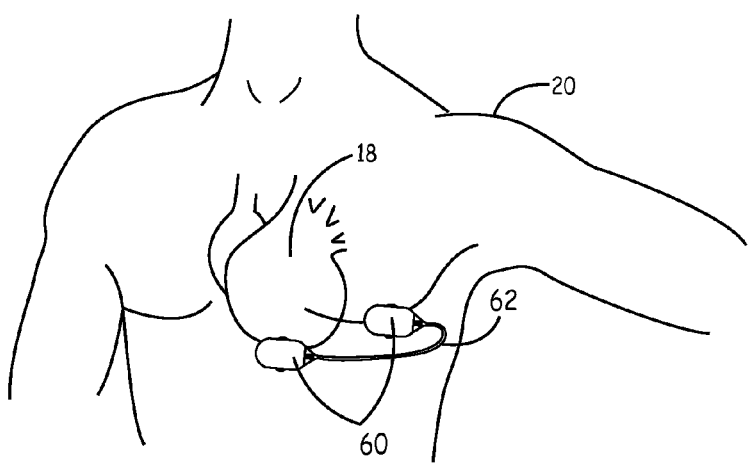

FIG. 5C illustrates SubQ ICD 60 implanted in patient 20. As discussed hereinabove, SubQ ICD 60 is subcutaneously implanted with the two housings carrying exposed large surface electrodes. The positioning is such that a major portion of the myocardium of heart 18 is located between the two electrodes 66 on each housing of SubQ ICD 60.

Figures 6A, 6B:
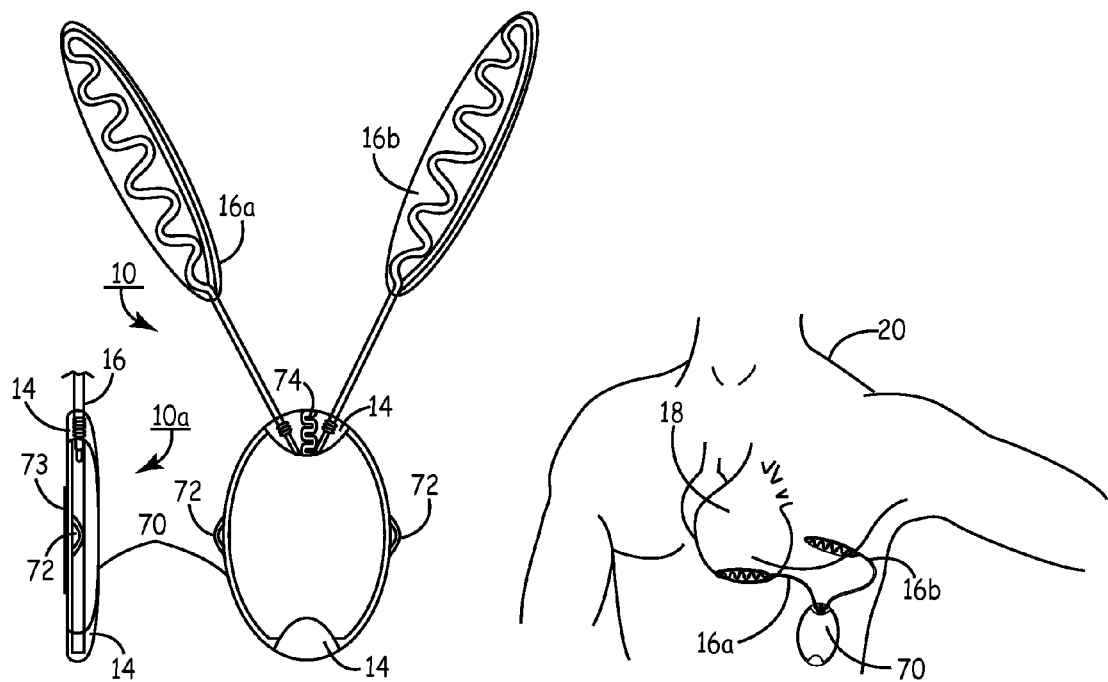
FIG. 6A illustrates a multi-planar view of the SubQ ICD in accordance with a sixth embodiment of the present invention.
FIGS. 6B, 6C and 6D illustrate SubQ ICD implant locations in a patient, a cross-sectional view of the thoracic cavity and the deployment of the SubQ ICD of the sixth embodiment, respectively.
Figures 6C, 6D:
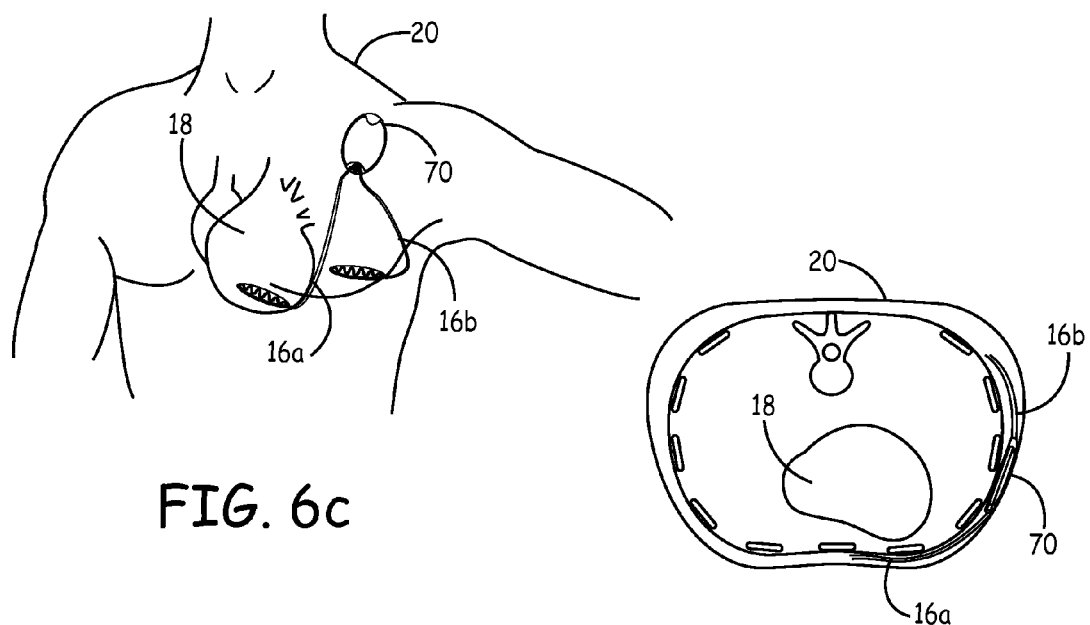

FIG. 6A illustrates a sixth embodiment of the present invention. SubQ ICD 70 is an ovaloid-shaped housing with connectors 14 for attaching 1, 2 or 3 subcutaneous sensing and cardioversion/defibrillation therapy delivery leads 16A and 16b. SubQ ICD 70 includes a connector on one end for attaching two subcutaneous leads and a second connector at the opposite end with capacity of attaching 1 subcutaneous lead. This design allows great flexibility in device placement and location. Elevation side view of SubQ ICD 70 shows the connector 14 and lead 16 attached. An active can electrode 73 allows sensing and cardioversion, defibrillation and/or pacing therapy delivery between the canister 70 and one or both leads 16A or 16b. An antenna 74 located in connector 14 allows RF telemetric programming control of SubQ ICD 70 and the uplinking of diagnostic data from device 70 to an external programmer (not shown) for physician review. Subcutaneous leads 16A and 16B form an electrode array. The electrode or pad carries an exposed large surface area with the electrodes forming a serpentine structure therein.

FIGS. 6B, 6C, 6D, 6E, 6F and 6G show various arrangements and subcutaneous implant locations of SubQ ICD 70. SubQ ICD 70 may be implanted adjacent the serratus anterior; adjacent the external abdominal oblique or adjacent the pectoralis major.

Figure 6H:
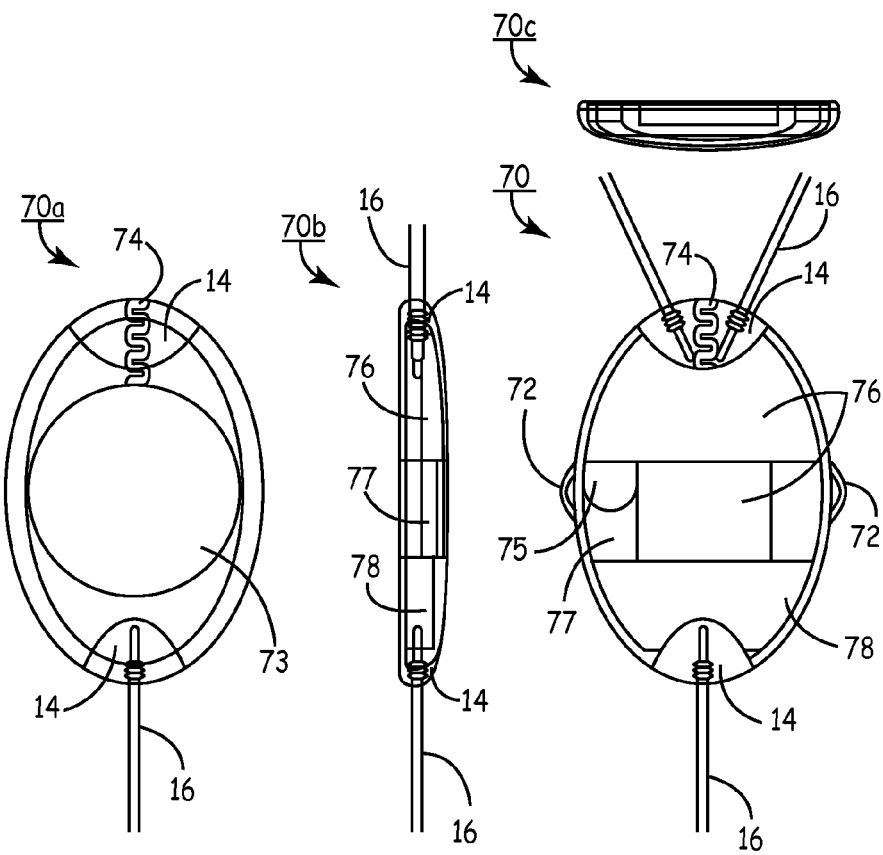
FIG. 6H illustrates a multi-planar view of an SubQ ICD in accordance with a seventh embodiment of the present invention.

FIG. 6H is a plan view showing the component parts/elements of the subcutaneous cardioverter-defibrillator of FIGS. 6A and 6e. View A is a top cut away view, view B is a bottom view, view C is a side cut away view and D is a center cross section view. Components shown include, battery 78, electronics module 77, capacitors 76, transformer 75, antenna 74, connector 14 (3 shown), lead 16 (3 shown), and active can electrode 73. Suture loops 72 are provided on housing 70 to allow the fixation as described hereinabove.

Figure 7A:
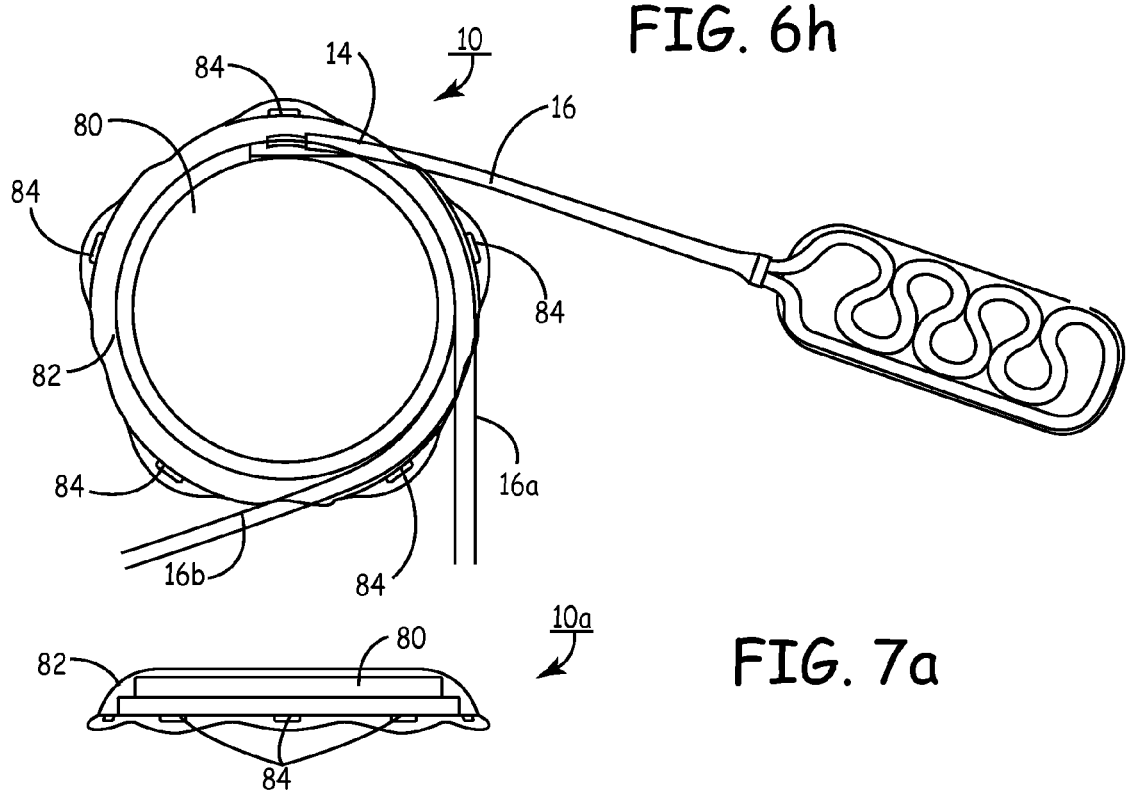
FIG. 7A illustrates a multi-planar view of the SubQ ICD of the seventh embodiment including an electrode array attached therewith.

FIG. 7A illustrates a seventh embodiment of the present invention. SubQ ICD 80 is a 2 diameter stepped round housing with connector 14 for attaching a subcutaneous sensing and cardioversion/defibrillation therapy delivery lead 16. SubQ ICD 80 may be constructed of stainless steel, titanium or ceramic. The electronics circuitry of SubQ ICD 80 may be incorporated in the manner described above. View 10A is a side view of the SubQ ICD 80 showing the 2 diameter stepped housing configuration with a flexible cover 82 to enable un-obtrusive subcutaneous implant of the canister following the contour of the natural curve of the patient's median ribcage at the cardiac notch. As discussed above, this structure also minimizes patient discomfort. Suture loops 84 are provided in flexible covering 82 to allow the fixation of the housing in a predetermined position for proper stimulation and to prevent device migration. Lead 16 may be wrapped in a groove around the housing 80 to "take up" excess lead length, thus minimizing patient discomfort and preventing chronic or potential pocket erosion (alternative lead exit locations shown at 16, 16A and 16b). Flexible cover 82 may be constructed of polyurethane, polyamide, polyetherether-ketone, polyether block amide, polytetrafluoroethylene, polyethylene, silicone or silastic.

Figure 7B:
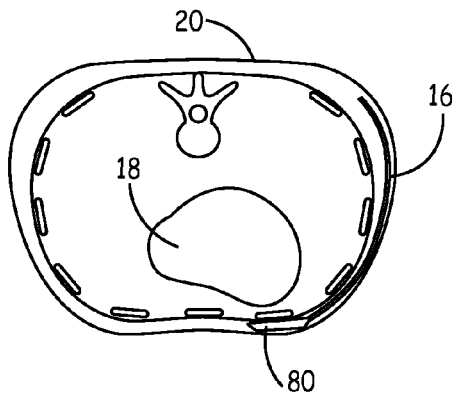
FIGS. 7B and 7C illustrate a cross-sectional view of the thoracic cavity and the deployment of the SubQ ICD and the SubQ ICD of the seventh embodiment implanted in a patient, respectively.
Figure 7C:
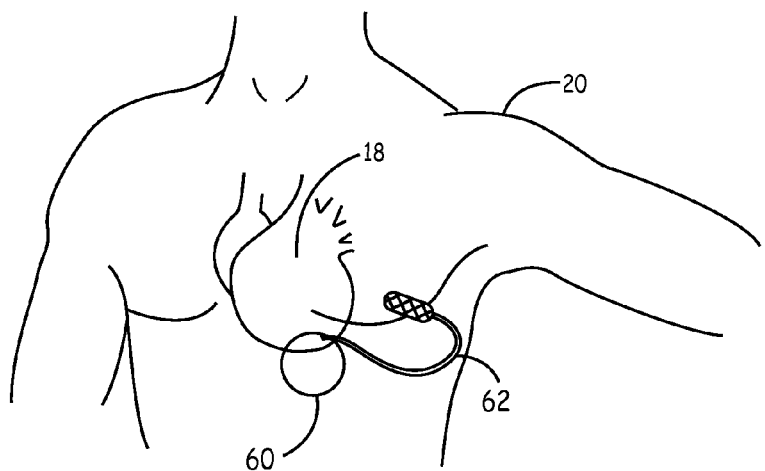

FIGS. 7B and 7C illustrate implant position of SubQ ICD 80 similar to the embodiments discussed hereinabove.

Figure 8A:
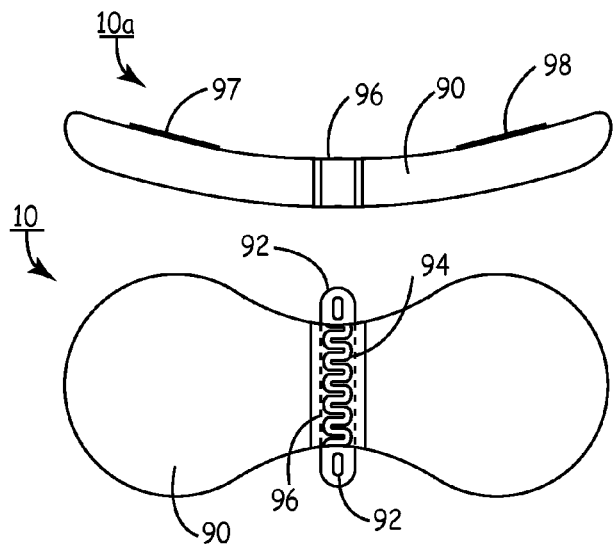
FIG. 8A illustrates a multi-planar view of an SubQ ICD in accordance with an eighth embodiment of the present invention.

FIG. 8A illustrates an eighth alternative embodiment of the present invention. SubQ ICD 90 is a segmented 2-lobe canister with integrated subcutaneous sensing and cardioversion/defibrillation therapy delivery electrodes 97 and 98. Canister 90 may be constructed of stainless steel, titanium or ceramic. The electronics circuitry of subcutaneous cardioverter-defibrillator 10 (described later in relation to FIG. 21) may be incorporated on a polyamide flex circuit, printed circuit board (PCB) or ceramic substrate with integrated circuits packaged in leadless chip carriers and/or chip scale packaging (CSP). View 10A is a top view of the housing 90 showing the segmented construction. Electrodes 97 and 98 located at opposite ends of SubQ ICD 90 are typically 100 mm$^2$ to 1000 mm$^2$. View 10A shows the ability of housing 90 to flexibly and dynamically assume a concave form to enable un-obtrusive subcutaneous implant. SubQ ICD tracks the natural curve of the patient's median to lateral ribcage from the cardiac notch. The segmented housing 90 allows physician flexibility in selecting implant locations and size and weight of patients for implant.

Figure 8B:
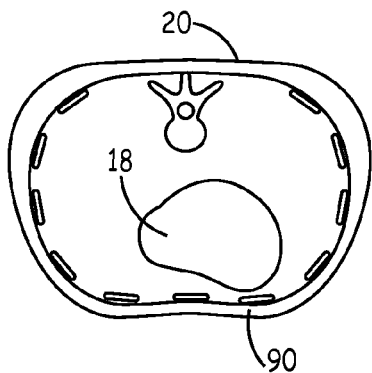
FIGS. 8B and 8C illustrate a cross-section view of the thoracic cavity and through the heart with the SubQ ICD deployed therein and the SubQ ICD of the eighth embodiment implanted in a patient, respectively.
Figure 8C:
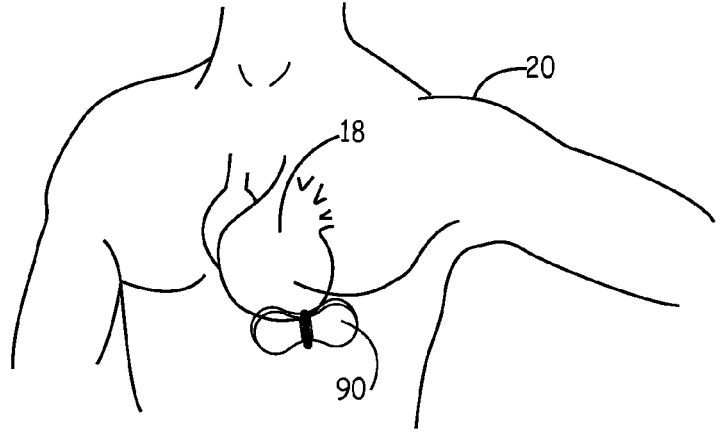

FIGS. 8B and 8C illustrate implant location of SubQ ICD 90 similar to the embodiments discussed hereinabove.

Figure 9A:
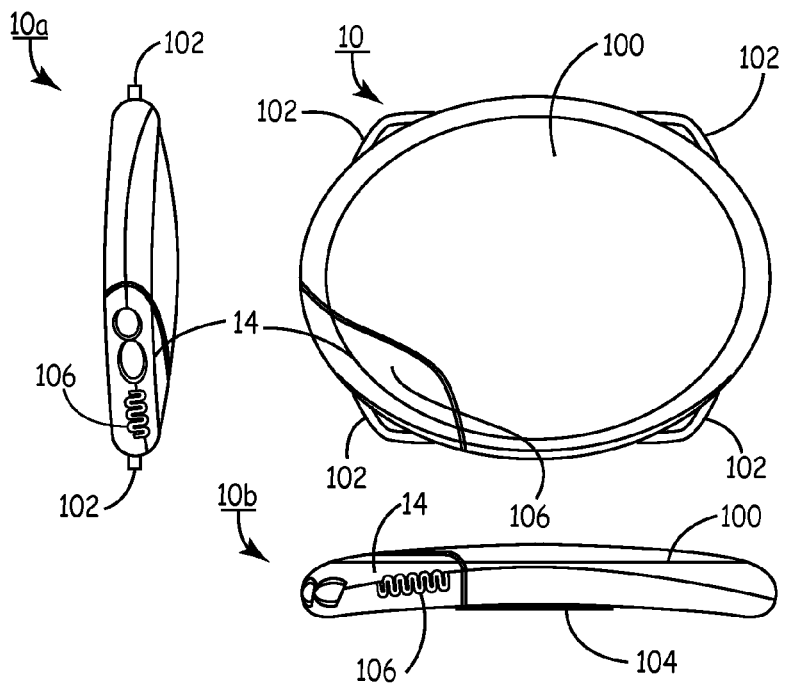
FIG. 9A illustrates a multi-planar view of the SubQ ICD of the ninth embodiment.

FIG. 9A is a plan side view of a subcutaneous cardioverter-defibrillator 10 of a ninth embodiment of the present invention. Canister 100 is an ovaloid-shaped housing with a connector 14 for attaching 1 or 2 subcutaneous sensing and cardioversion/defibrillation therapy delivery leads. This design allows great flexibility in device placement and location. Canister 100 may be constructed of stainless steel, titanium or ceramic. The electronics circuitry of subcutaneous cardioverter-defibrillator 10 (described later in relation to FIG. 21) may be incorporated on a polyamide flex circuit, printed circuit board (PCB) or ceramic substrate with integrated circuits packaged in leadless chip carriers and/or chip scale packaging (CSP). View 10A is an end view of subcutaneous cardioverter-defibrillator 100 showing the connector 14, suture loops 102 (2 shown) and antenna 106. Suture loops 102 are provided on housing 100 to allow the fixation of housing in a fixed pocket location for proper stimulation and to prevent device migration. View 10B is a side view of SubQ ICD cardioverter-defibrillator 100 showing the concave inner surface, connector 14, active can electrode 104 and antenna 106. The concave inner surface of SubQ ICD 100 enables a smooth deployment in the subcutaneous above the ribs. An antenna 106 located in the connector 14 allows RF telemetric programming control of SubQ ICD 100 and the uplinking of diagnostic data from device 100 to an external programmer (not shown) for physician review.

Figure 9B:
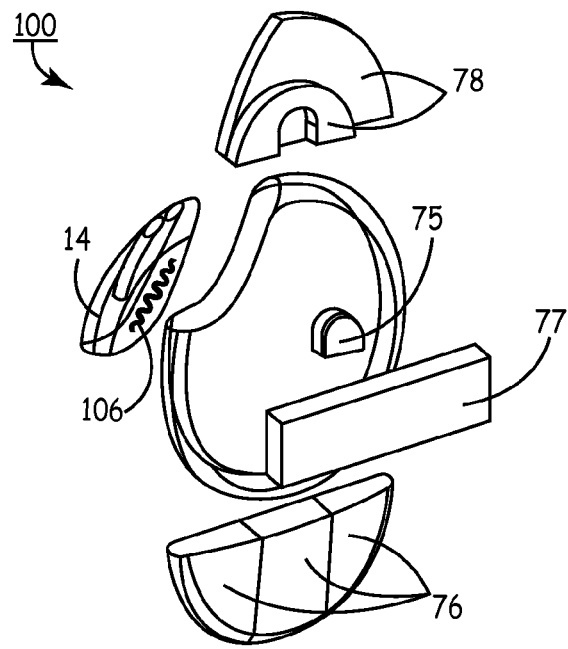
FIGS. 9B and 9C illustrates perspective views of a SubQ ICD showing major internal piece parts of a generic embodiment.

FIG. 9B is a plan view showing the component parts/elements of the SubQ ICD 100 of FIG. 9A. Components shown include, battery 77, electronics module 76, tantalum capacitors 76 (3 shown), transformer 75, antenna 106 and connector 14.

Figure 9C:
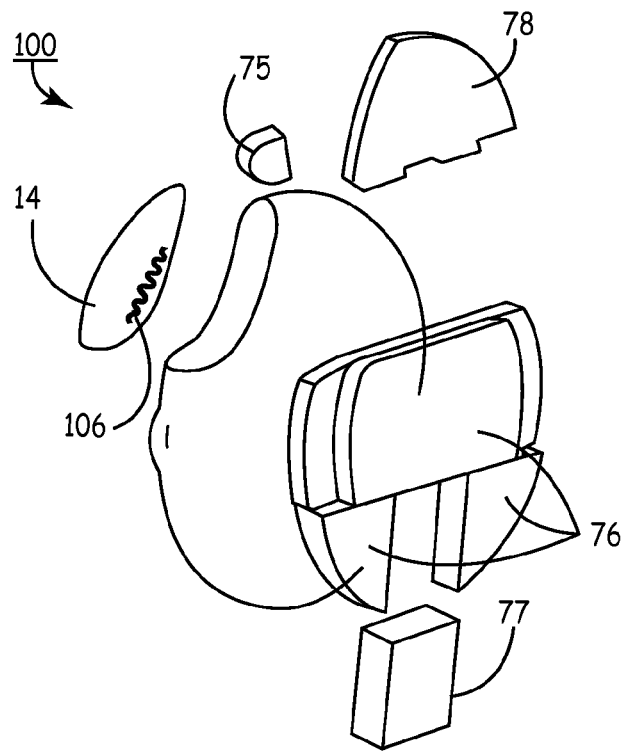
Figure 9D:
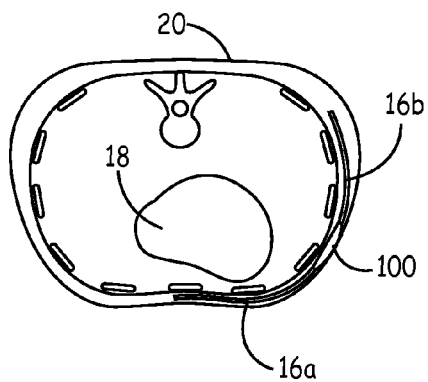
FIG. 9D-9I illustrate a cross-sectional view of the thoracic cavity and section through the heart illustrating various lead, electrodes and SubQ ICD of the eighth embodiment deployed in various positions and configurations.
Figure 9E:
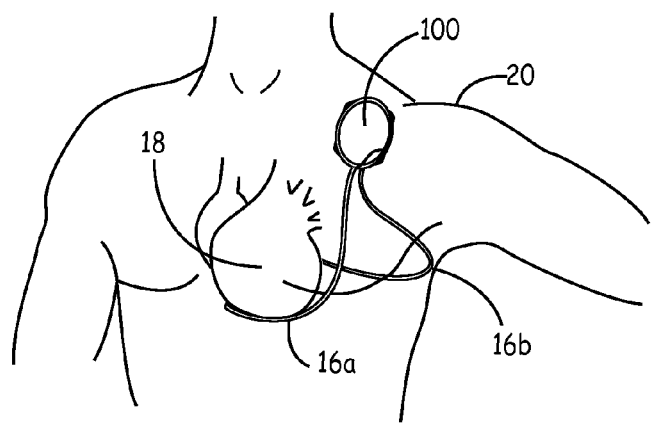
Figure 9F:
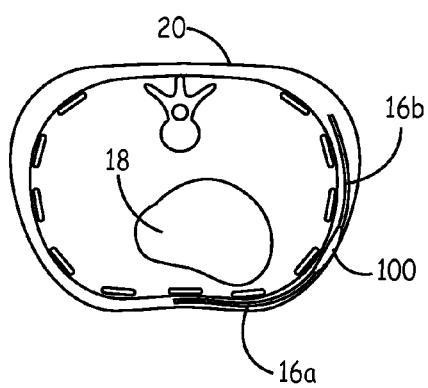
Figure 9G:
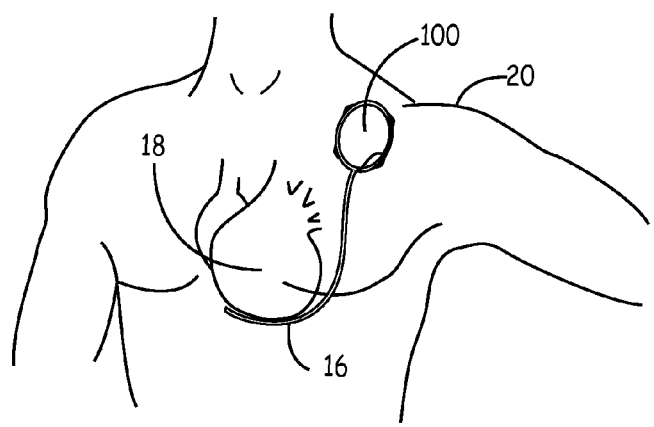
Figure 9H:
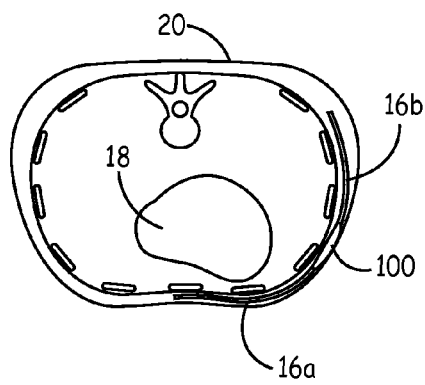
Figure 9I:
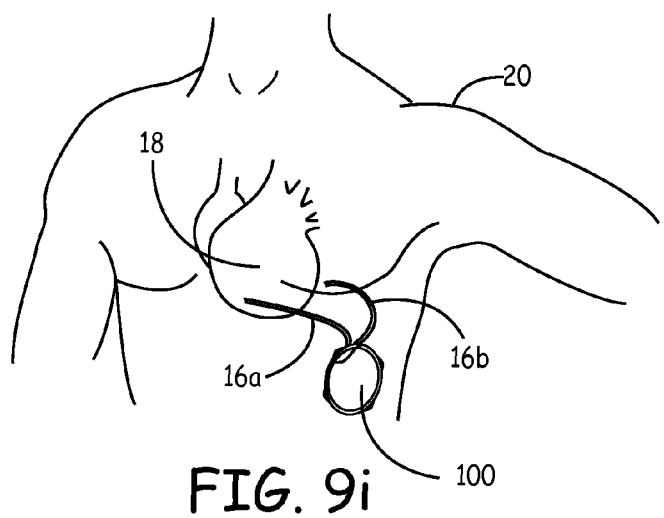
Figure 9J:
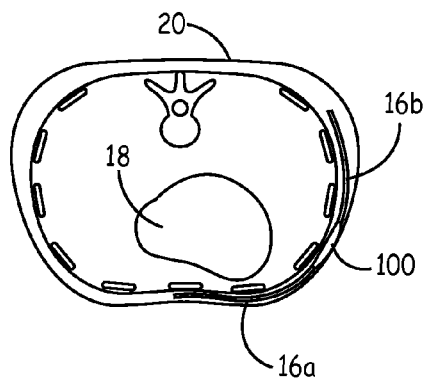
FIGS. 9J and 9K illustrate a cross-sectional view of the thoracic cavity and through the heart with a SubQ ICD deployed therein and the SubQ ICD of the eighth embodiment implanted in a patient, respectively.
Figure 9K:
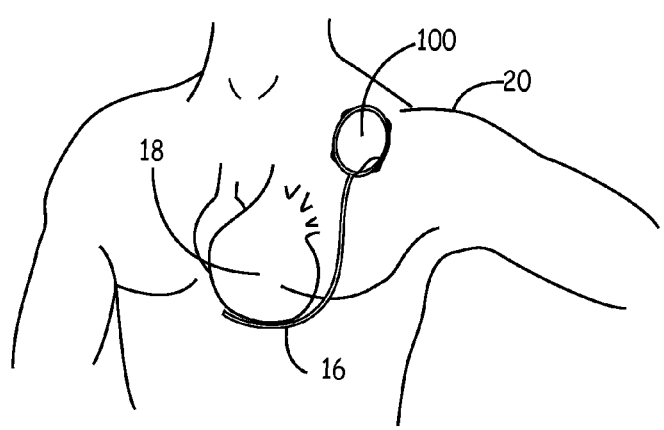
Figure 9L:
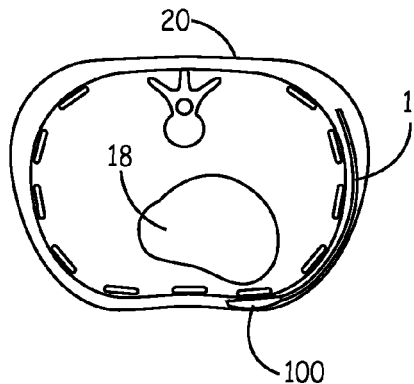
FIGS. 9L and 9M illustrate a cross-sectional view of the thoracic cavity and through the heart with a SubQ ICD of the eighth embodiment deployed therein and the SubQ ICD implanted in a patient, respectively.
Figure 9M:
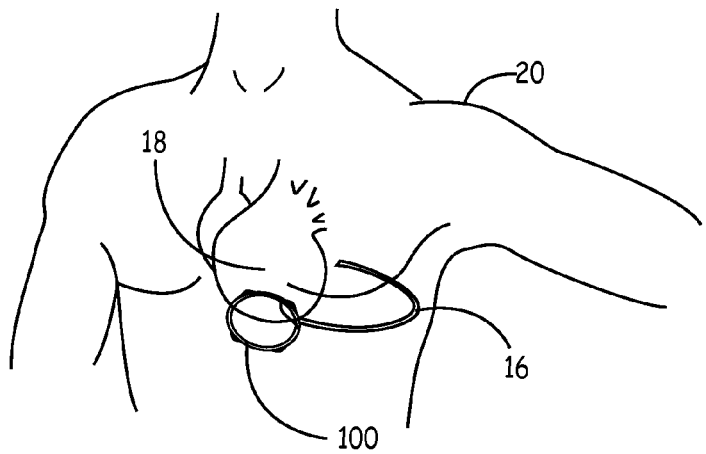

FIG. 9C is a perspective view showing an alternative embodiment of the major piece parts/elements of the SubQ ICD 100 of FIG. 9A. Components shown include, battery 77, electronics module 78, aluminum capacitors 76 (4 shown), transformer 75, antenna 106 and connector 14.

FIGS. 9D-9M illustrate various implant locations of SubQ ICD 100. Specifically, pectoral serratus anterial, cardiac notch and sternum implant positions for SubQ ICD 100 are shown. Further, single and dual lead configurations are implemented with SubQ ICD 100. As illustrated, an active can with one or two leads is implanted as shown in various locations outside the thoracic cavity. Similarly, a non-active SubQ ICD 100 with two leads coupled therewith is implanted in various parts subcutaneously outside the thoracic cavity.

Figure 10A:
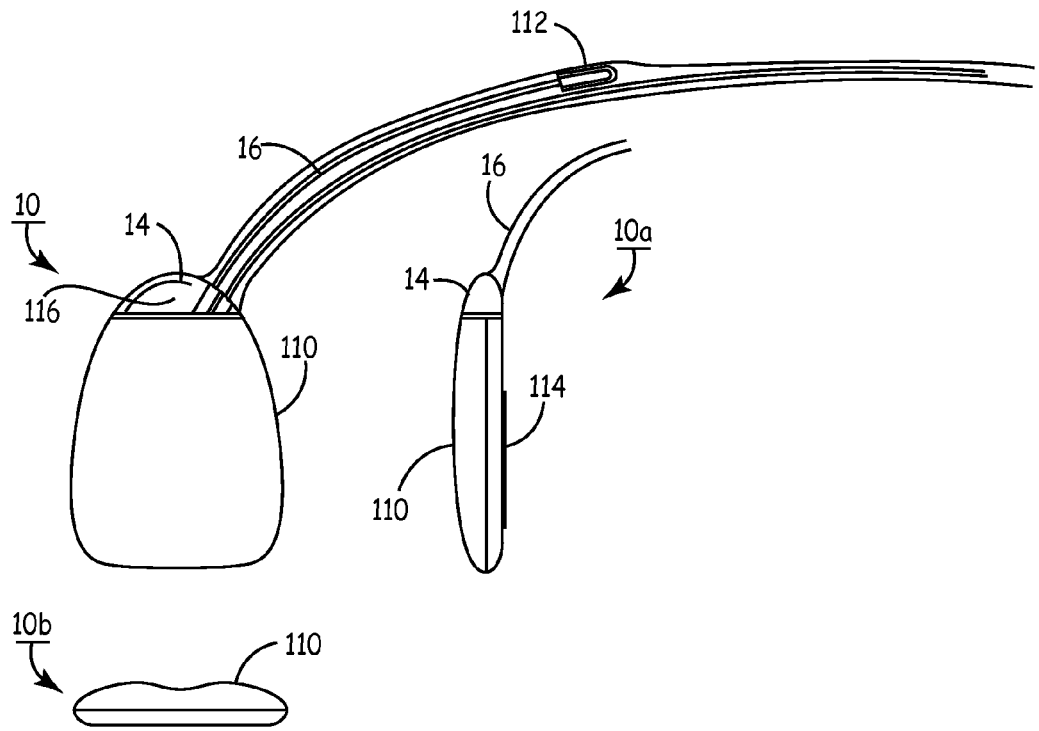
FIG. 10A illustrates a multi-planar view of a SubQ ICD of a tenth embodiment.

FIG. 10A is a plan side view of a SubQ ICD 110 of a tenth embodiment of the present invention. SubQ ICD 110 is a rounded triangular shaped canister with connector 14 for attaching a subcutaneous sensing and cardioversion/defibrillation therapy delivery lead 16 with an integrated proximal second electrode. SubQ ICD 110 may be constructed of stainless steel, titanium or ceramic. The electronics circuitry of subcutaneous cardioverter-defibrillator 10 (described later in relation to FIG. 21) may be incorporated on a polyamide flex circuit, printed circuit board (PCB) or ceramic substrate with integrated circuits packaged in leadless chip carriers and/or chip scale packaging (CSP). View 10A is a side view of SubQ ICD 110 showing the connector 14, lead 16 and active can area electrode 114. The active can electrode 114 allows sensing and cardioversion, defibrillation and/or pacing therapy delivery between the canister 110 and one or both electrodes on subcutaneous lead 16. The active can electrode is typically 100 mm² to 1000 mm² in active area. View 10B is a horizontal side view of the SubQ ICD 110 showing the thin rounded construction subcutaneous implant. The thin rounded housing construction allows physician flexibility in selecting implant locations while enabling adjustability for size and weight of patients for implant. This structure also provides ergonomic compatibility and patient comfort during normal movement of the thoracic muscles and frame.

Figure 10B:
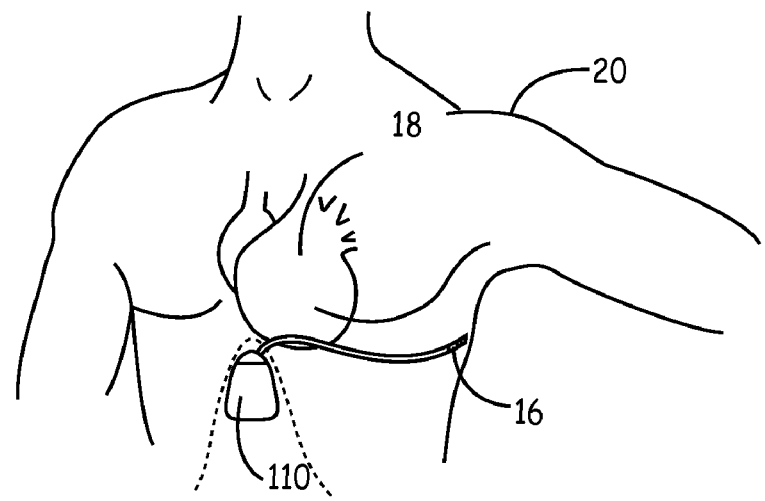
FIG. 10B illustrates the SubQ ICD of the ninth embodiment implanted in a patient.

FIG. 10B illustrates implant location of SubQ ICD 110 and subcutaneous lead 16 similar to the relevant embodiments discussed hereinabove.

Figure 11A:
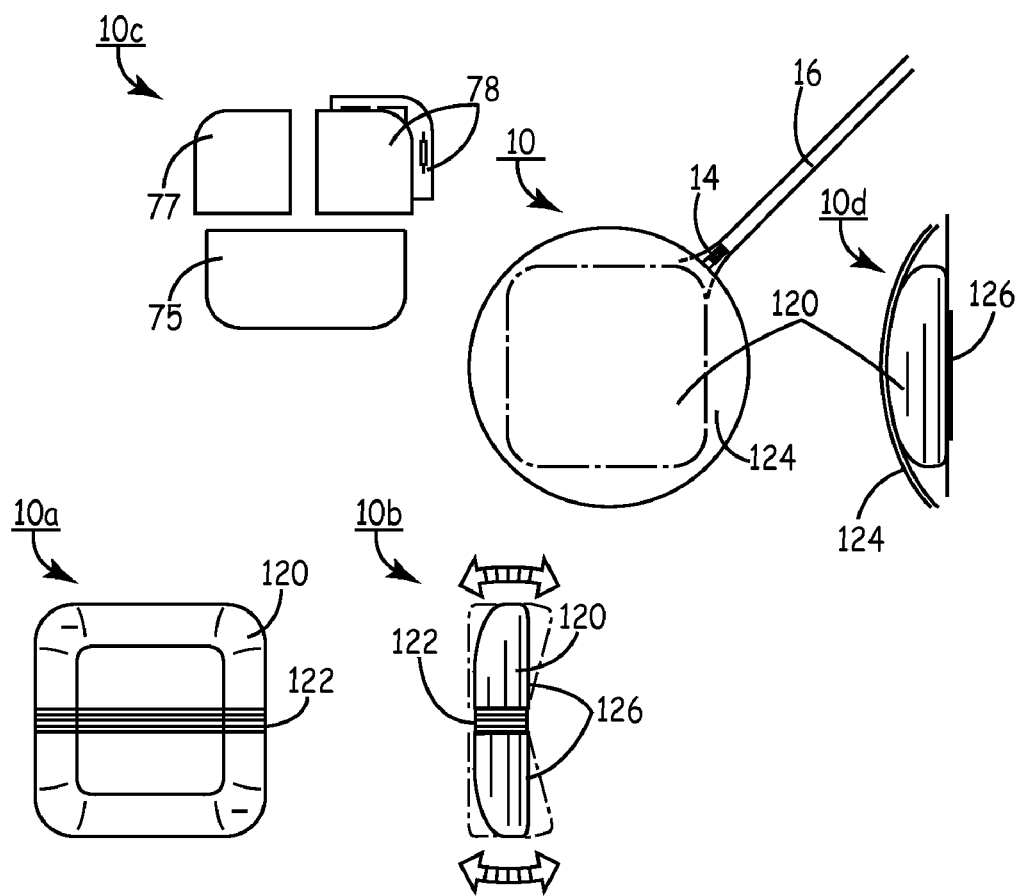
FIG. 11A illustrates a multi-planar view of a SubQ ICD of the eleventh embodiment.

FIG. 11A is a plan side view of a subcutaneous cardioverter-defibrillator 10 of an eleventh alternative embodiment of the present invention. SubQ ICD 120 is a segmented rounded square-shaped canister with a connector 14 for attaching a subcutaneous sensing and cardioversion/defibrillation therapy delivery lead 16. SubQ ICD 120 may be constructed of stainless steel, titanium or ceramic. The electronics circuitry of subcutaneous cardioverter-defibrillator 10 (described later in relation to FIG. 21) may be incorporated on a polyamide flex circuit, printed circuit board (PCB) or ceramic substrate with integrated circuits packaged in leadless chip carriers and/or chip scale packaging (CSP). View 10A is a view of SubQ ICD 120 showing the segmented center section 122 to allow adjusting of the concave inner surface of SubQ ICD 120 (see view 10B). View 10B is a side view of SubQ ICD 120 showing the concave inner surface and active can electrode 126. The adjustable concave inner surface of SubQ ICD 120 provides east of and further enables the canister to follow the natural curve of the patient's ribcage and pectoral regions. View 10D is a side cut-away view of subcutaneous cardioverter-defibrillator 10 showing the round flexible cover 124 and active can electrode 126. Flexible cover 124 may be constructed of polyurethane, polyamide, polyetherether-ketone, polyether block amide, polytetrafluoroethylene, polyethylene, silicone or silastic.

Figure 11B:
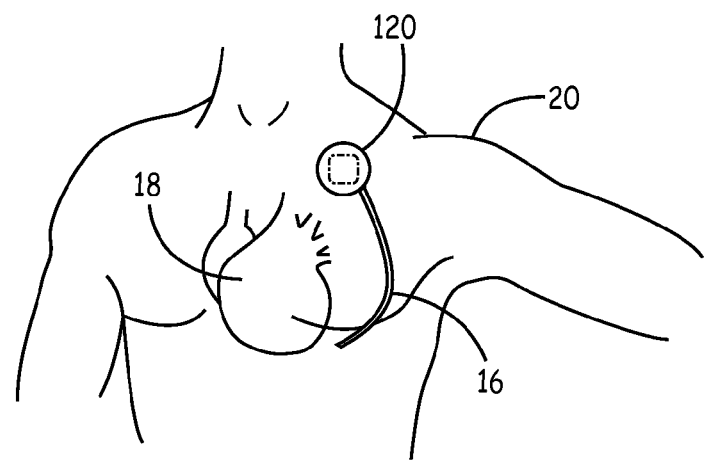
FIG. 11B illustrates the SubQ ICD of the eleventh embodiment implanted in a patient.

FIG. 11B illustrates SubQ ICD 120 of FIG. 11A subcutaneously implanted pectorially and 1 subcutaneous sensing and cardioversion/defibrillation therapy delivery lead 16 in relation to the heart 18. The subcutaneous lead 16 is tunneled subcutaneously from the implant pocket of device 120 inferiorly to a location near the cardiac notch such that the heart 18 is disposed between the distal end of subcutaneous lead 16 and the housing 120. The implant location of device 120 is typically between the $1^{st}$ and 3rd ribs and lead 16 is typically implanted between the 3rd and 8th ribs.

Figure 12A:
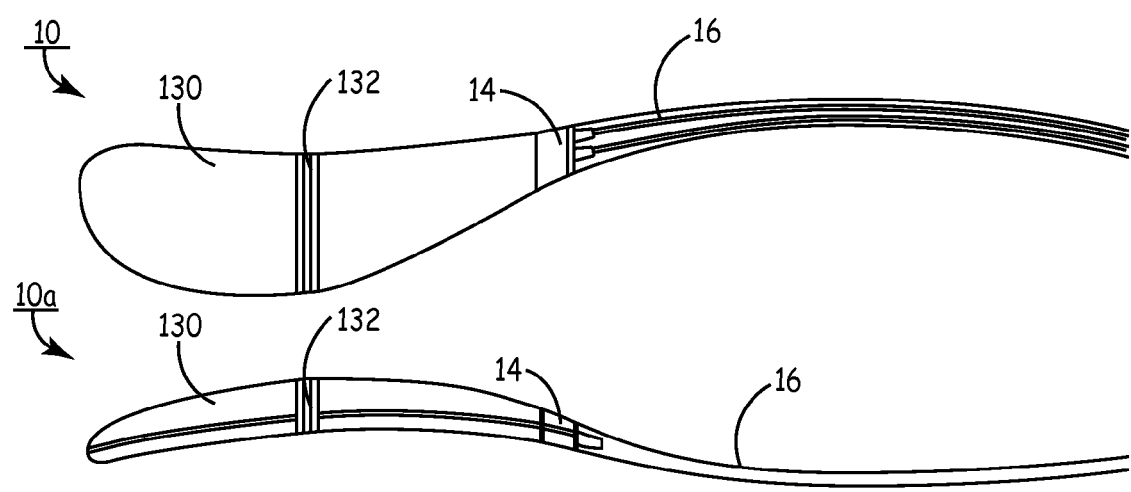
FIG. 12A illustrates a multi-dimensional view of an SubQ ICD of an twelfth embodiment.

FIG. 12A illustrates SubQ ICD 130 of a twelfth embodiment of the present invention. SubQ ICD 130 is a concave segmented extended ovaloid-shaped canister with flexible segment 132 and connector 14 for attaching a subcutaneous sensing and cardioversion/defibrillation therapy delivery lead 16. View 10A is a top view of the SubQ ICD 130 showing the adjustable concave construction. The various innovative aspects of the shape and its ergonomic features are similar to those discussed above.

Figure 12B:
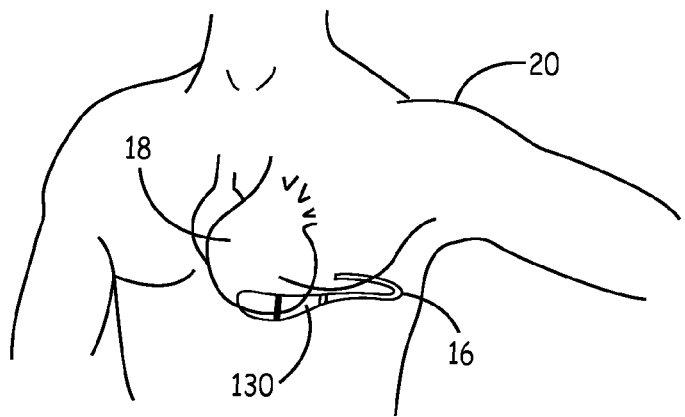
FIG. 12B illustrates a SubQ ICD of the twelfth embodiment implanted in a patient.

FIG. 12B illustrates SubQ ICD 130 subcutaneously implanted outside a patient's 20 ribcage anterior to the cardiac notch and a subcutaneous sensing and cardioversion/defibrillation therapy delivery lead 16 in relation to the heart 18. With the exception of the shape and the distinguishing features, the implant position and arrangements including the functionality of the device and the subcutaneous lead is similar to complementary arrangements discussed above.

Figure 13A:
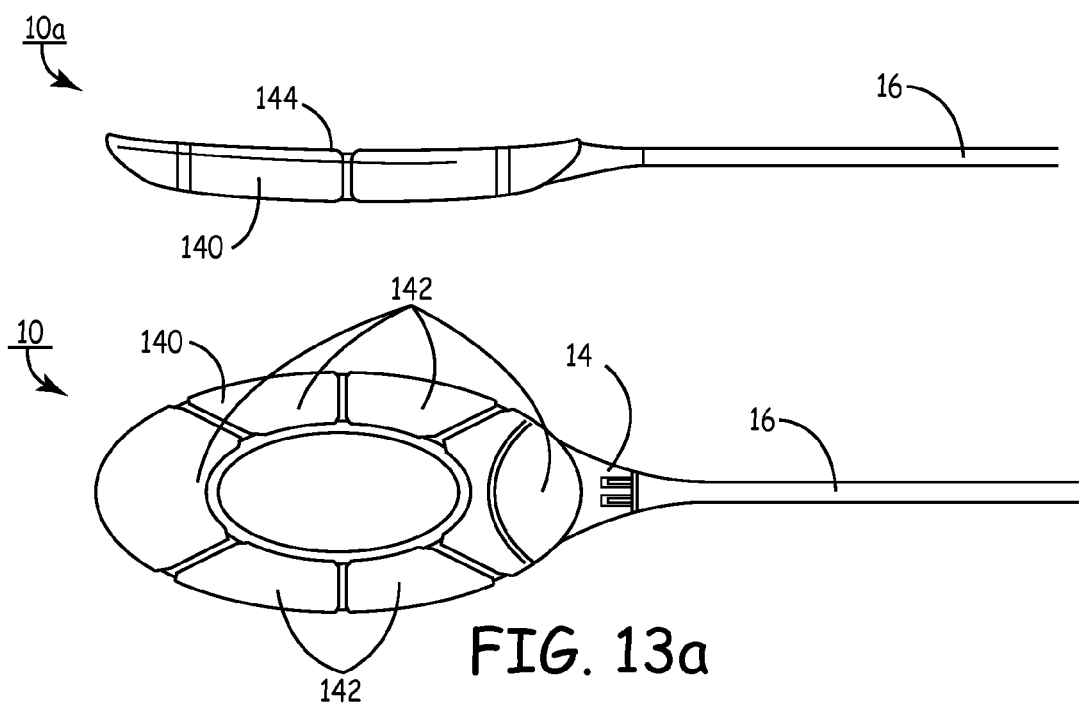
FIG. 13A illustrates a multi-planar view of a SubQ ICD of a thirteenth embodiment.

FIG. 13A illustrates a SubQ ICD 140 in accordance with the thirteenth embodiment of the present invention. SubQ ICD 140 is a concave segmented ovaloid-shaped canister with multiple flexible segments 142 and connector 14 for attaching a subcutaneous sensing and cardioversion/defibrillation therapy delivery lead 16. SubQ ICD 140 may be constructed of stainless steel, titanium or ceramic. View 10A of SubQ ICD 140 shows the shape factors that enable east of implant and adaptability to the rib structure as discussed in complementary sections hereinabove.

Figure 13B:
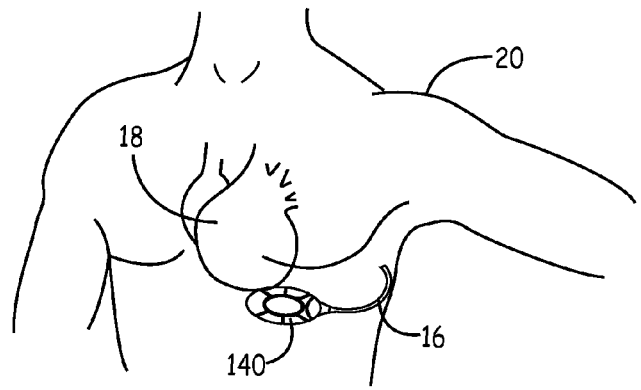
FIG. 13B illustrates a SubQ ICD of the thirteenth embodiment implanted in a patient.

FIG. 13B illustrates SubQ ICD 140 implanted outside a patient's 20 ribcage anterior to the cardiac notch and a subcutaneous sensing and cardioversion/defibrillation therapy delivery lead 16 in relation to the heart 18. The implant arrangement and location as shown is similar to complementary disclosures hereinabove.

Figure 14A:
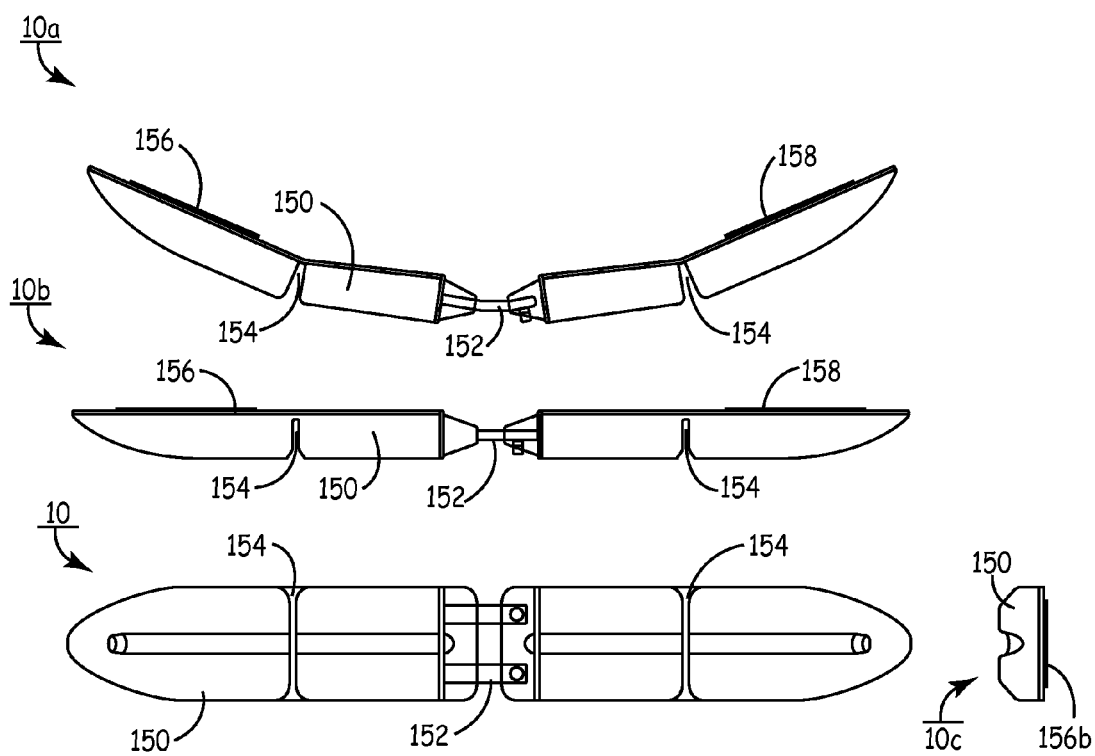
FIG. 14A illustrates a multi-planar view of a SubQ ICD of a fourteenth embodiment.

FIG. 14A is a plan side view of SubQ ICD 150 of a fourteenth embodiment of the present invention. SubQ ICD 150 is an elongated segmented 2-piece pointed oval housing with integrated subcutaneous sensing and cardioversion/defibrillation therapy delivery electrodes 156 and 158. With exception of the shape, the material of construction, piece parts and electronics are similar to complementary SubQ ICD embodiments discussed hereinabove.

Figure 14B:
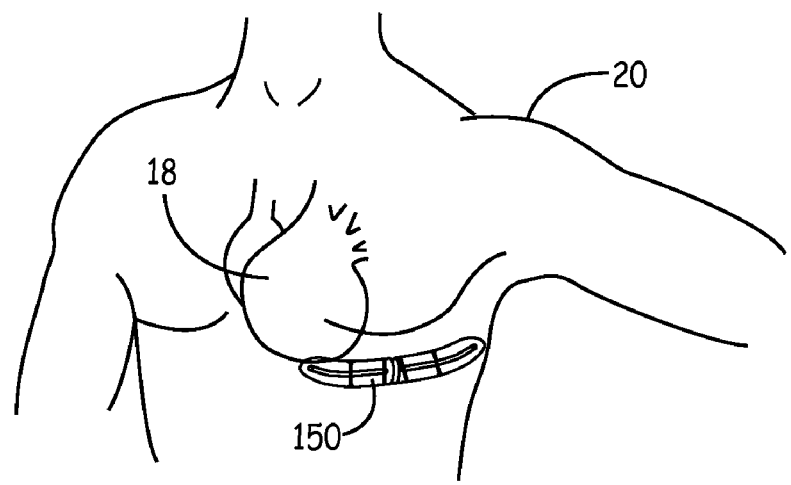
FIG. 14B illustrates a SubQ ICD of the fourteenth embodiment implanted in a patient.

FIG. 14B illustrates SubQ ICD 150 subcutaneously implanted outside a patient's 20 ribcage with electrode 156 anterior to the cardiac notch and the housing 150 is tunneled and positioned such that electrode 158 is laterally positioned in relation to the heart 18.

Figure 14C:
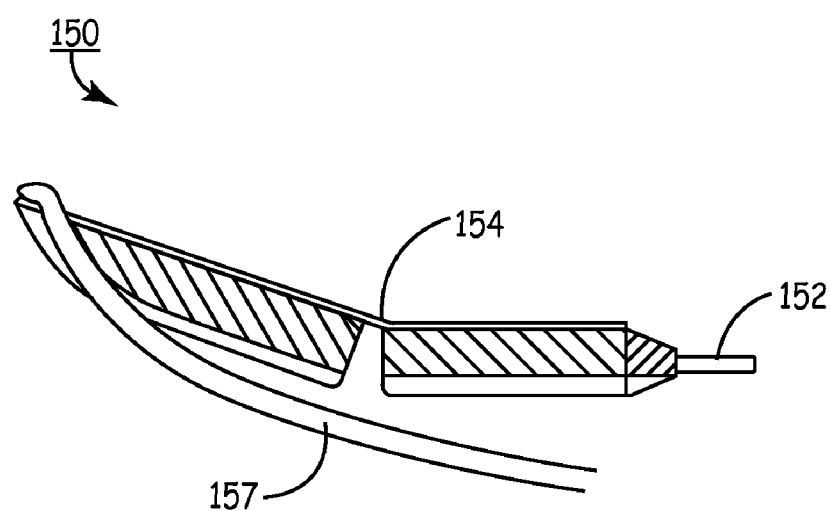
FIG. 14C illustrates a cross-sectional view of a SubQ ICD of the fourteenth embodiment.

FIG. 14C is a plan view of a method of implant for SubQ ICD 150 shown in FIG. 14A. At the implant incision lateral to the cardiac notch, half of the housing 150 is tunneled toward the cardiac notch with implant tool 157. Upon inserting half of the housing to its final site, the implant tool is disconnected from the housing and removed. The remaining half of the housing is then inserted in the same manner in an opposite direction from the same implant site. When both halves are inserted, they are connected together at connector 152.

Figure 15A:
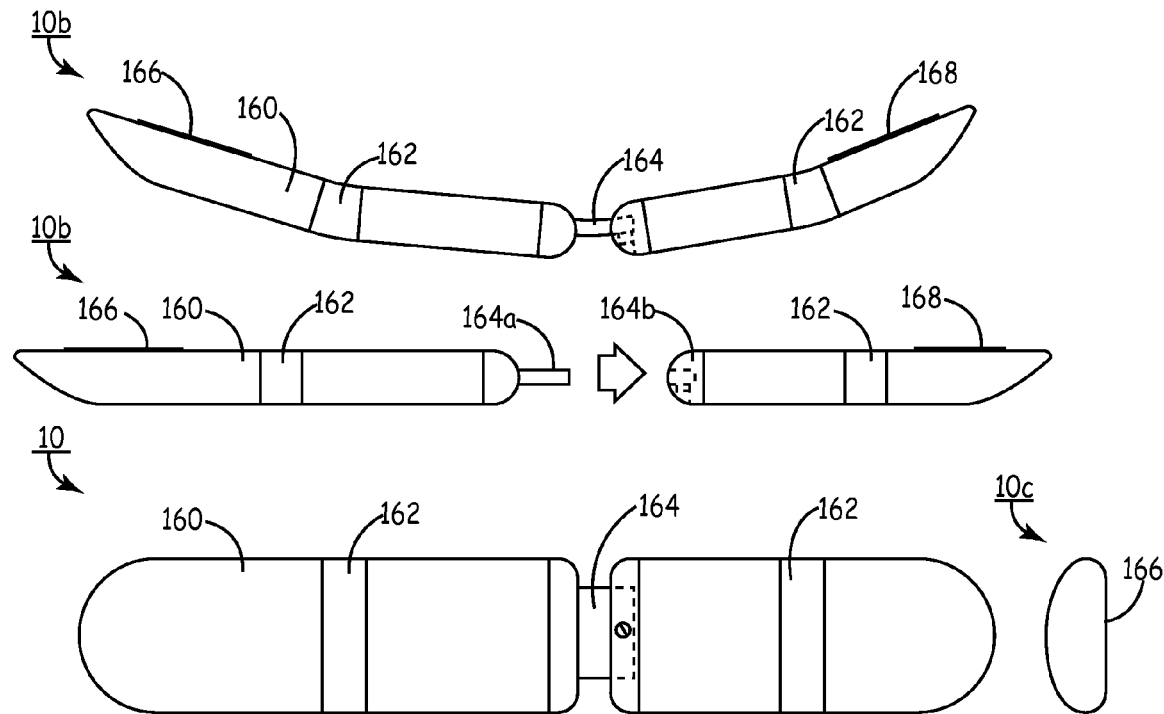
FIG. 15A illustrates a multi-planar view of a SubQ ICD of a fifteenth embodiment.

FIG. 15A illustrates a SubQ ICD 10 of a fifteenth alternative embodiment of the present invention. SubQ ICD 160 is an elongated segmented 2-piece rounded oval housing with integrated subcutaneous sensing and cardioversion/defibrillation therapy delivery electrodes 166 and 168. The central section 164 allows the 2 halves of housing 160 to be separated while the 2 flexible segments 162 allow the housing 160 to form a variable concave form. Electrodes 166 and 168 located at opposite ends of canister 160 are typically 100 mm$^2$ to 1000 mm$^2$.

Figures 15B, 15C:
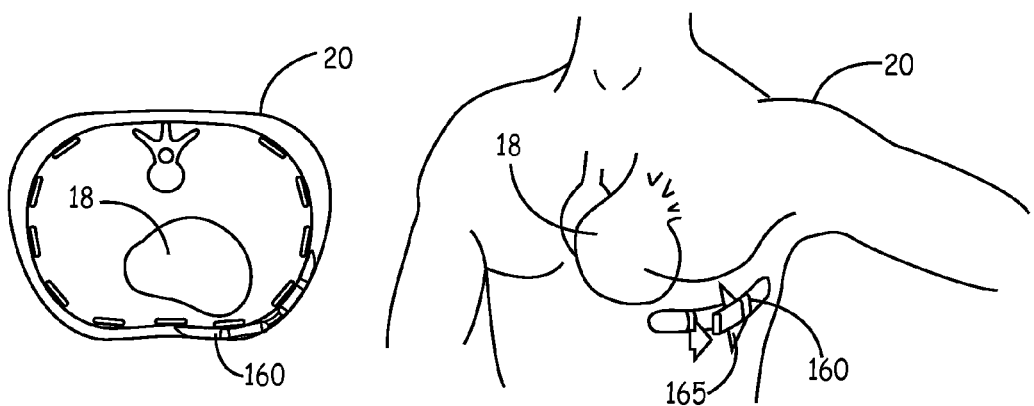
FIGS. 15B and 15C illustrate a cross-sectional view of a thoracic cavity and through the heart with a SubQ ICD deployed therein and the SubQ ICD of the fifteenth embodiment implanted in a patient, respectively.

FIG. 15B illustrates a SubQ ICD 160 implanted in a patient. The configuration and location with the exception of the innovative shape of SubQ ICD 160, are similar to complementary disclosures hereinabove.

FIG. 15C illustrates SubQ ICD 160 of FIG. 14A subcutaneously implanted outside a patient's 20 ribcage with electrode 166 anterior to the cardiac notch and the housing 160 is inserted in an incision 165 and is tunneled and positioned such that electrode 168 is laterally positioned in relation to the heart 18. The implant location of device 160 is typically between the $3^{rd}$ and $8^{th}$ ribs. At the implant incision 165 lateral to the cardiac notch, half of the housing 160 is tunneled toward the cardiac notch. The remaining half of the housing 160 is then inserted in the same manner in an opposite direction from the same implant site 165. When both halves are inserted, they are connected together at connector 164.

Figure 16:
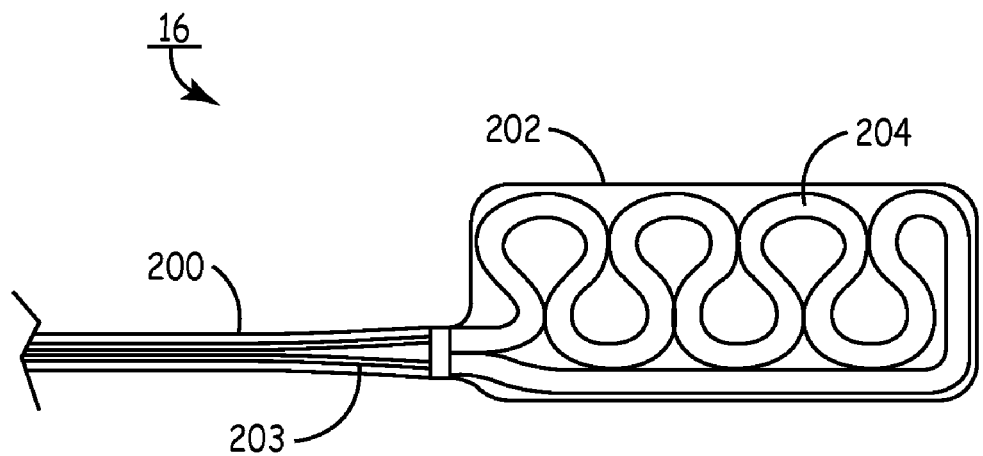
FIG. 16 illustrates an embodiment of a subcutaneous lead with a serpigenous electrode array.

FIG. 16 illustrates subcutaneous sensing and cardioversion-defibrillation therapy delivery lead 16 to be used in conjunction with the SubQ ICD of FIG. 1A, 2A, 6A, 6E, 7A, 9A, 10A, 11A, 12A, or 13A. Lead 200 includes a conductor 203 and a distal serpentine electrode coil 204 arrayed on a rectangular or, alternatively, an oval shaped flexible mesh. The electrode may be constructed of titanium, nickel alloys, stainless steel, platinum, platinum iridium and/or mixtures of this list.

Figure 17:
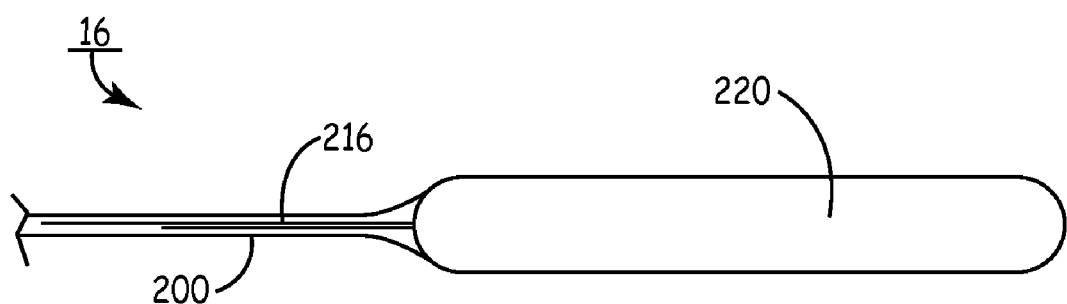
FIG. 17 illustrates an embodiment of a subcutaneous lead with a mesh electrode array.

FIG. 17 illustrates an alternative embodiment of a subcutaneous sensing and cardioversion-defibrillation therapy delivery lead 200 for use with the SubQ ICD of FIG. 1A, 2A, 6A, 6E, 7A, 9A, 10A, 11A, 12A, or 13A. Lead 200 is constructed of a lead body including a conductor 216 and a distal titanium mesh electrode 220.

Figure 18:
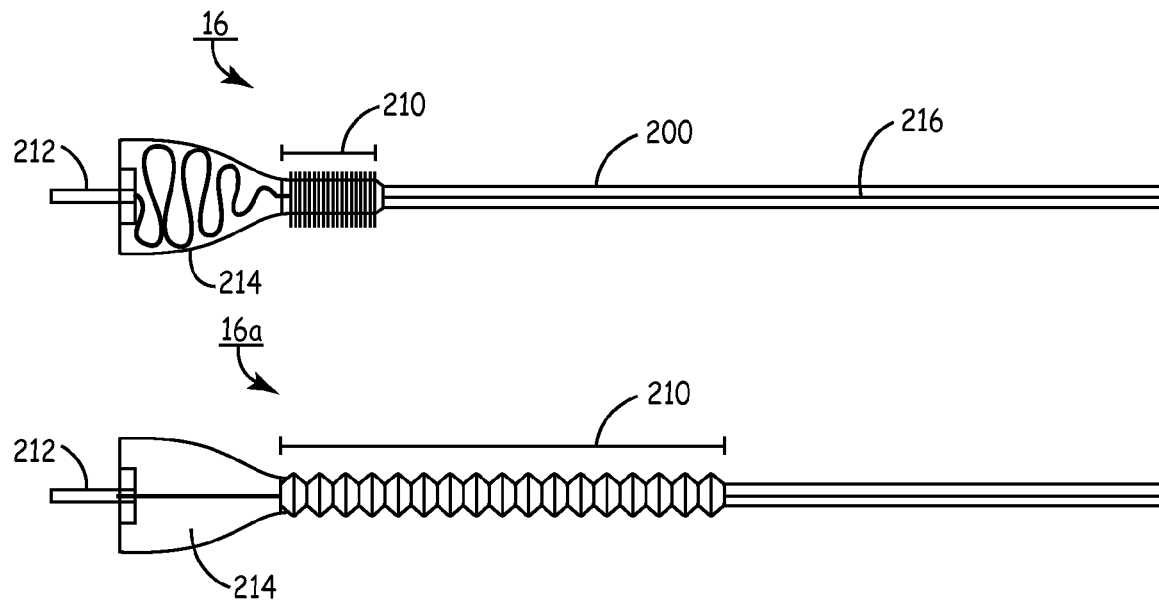
FIG. 18 illustrates a telescoping and extensible subcutaneous lead.

FIG. 18 illustrates another alternative embodiment of a subcutaneous sensing and cardioversion-defibrillation therapy delivery lead to be used in conjunction with the subcutaneous cardioverter-defibrillator of FIG. 1A, 2A, 6A, 6E, 7A, 9A, 10A, 11A, 12A, or 13A. View L shows the proximal end of lead 16 with proximal connector pin 212, proximal boot 214, conductor 216 and a collapsed proximal boot extension 210 for containing excess lead length, which may be deployed by pulling on the lead to lengthen conductor 216. View 16A shows the lead 200 with lead boot extension 210 extended to maximal length.

Figure 19:
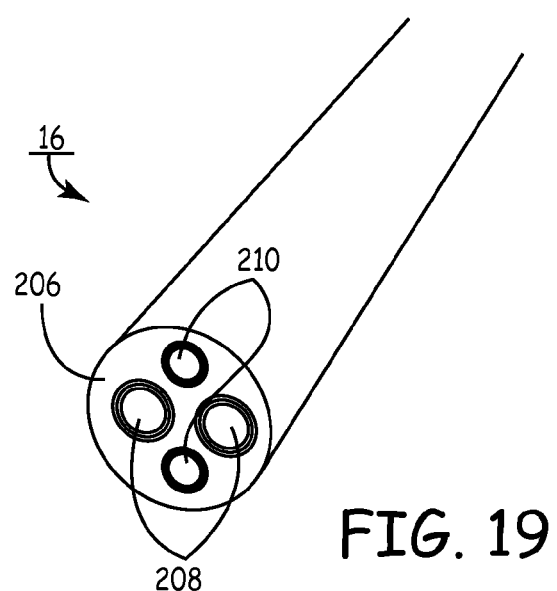
FIG. 19 illustrates a cross-sectional view through the lead body of FIG. 18.

FIG. 19 shows a cross section view of the lead body 200 for subcutaneous sensing and cardioversion-defibrillation therapy delivery lead as shown in FIGS. 17 and 18. The lead body consists of insulation 236 of HP Silicone. The defibrillation conductors 234 are constructed of Ag/MP35N and wrapped with ETFE and reinforced with tensile material. The sensing conductors are wrapped with ETFE.

Figure 20:
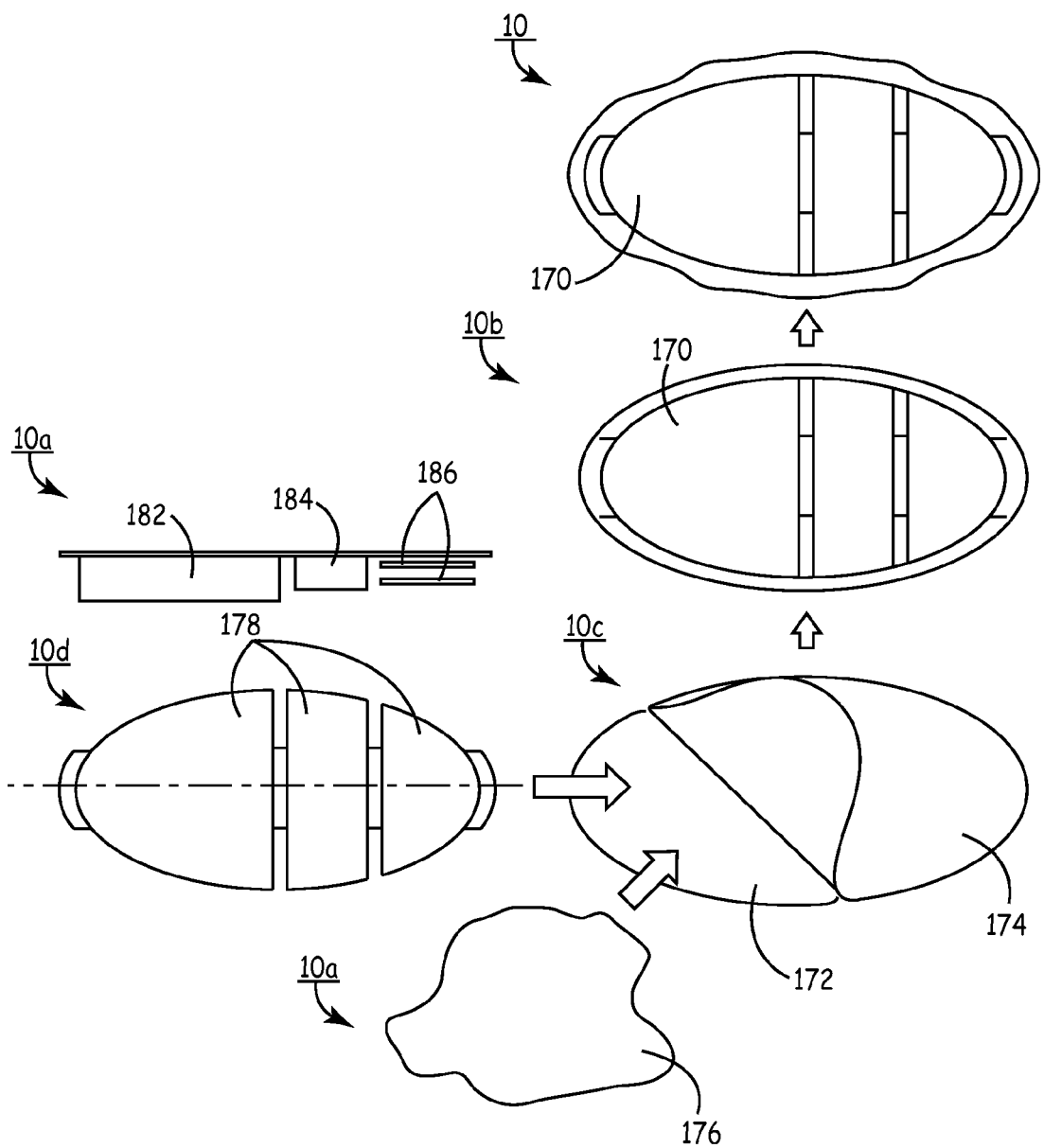
FIG. 20 illustrates a multi-planar view of a SubQ ICD of a fifteenth embodiment.

FIG. 20 illustrates an assembly method of a flexible segmented SubQ ICD 10 as shown above in relation to FIGS. 2A, 3A, 8A, 11A, 12A, 13A, 14A and 15A. View 10A is a cross sectional side view of the components in housing 170 showing capacitors 182, battery 184 and electronics module 186 mounted on a flex circuit 180. View 10D is a top view of housing 170 showing the segmented construction; with individuals encapsulated modules 178 mounted on flex circuit 180. The module of view 10d is inserted into an envelope consisting of a top 174 and bottom 172 flexible insulating material and a flexible insulating gel 176 (view 10c) and sealed therein (view 10b). View 10 illustrates that the shape of canister 170 assumes the volume and shape of the implant pocket of the patient it is implanted in. This configuration enables a smooth minimally invasive subcutaneous implant of the SubQ ICD following the natural curve of the patient's ribcage and naturally fills the irregular volume and shape of the implant pocket. This allows physician flexibility in accommodating patient variance in size and weight while providing all the other advantages discussed in similar complementary embodiments hereinabove.

The electronic circuitry employed in the SubQ ICD (as described above in relation to the various embodiments shown in FIG. 1-15) can take any of the known forms that detect a tachyarrhythmia from the sensed EGM and provide cardioversion/defibrillation shocks as well as post-shock pacing as needed. A simplified block diagram of such circuitry adapted to function employing the first and second and, optionally, the third cardioversion-defibrillation electrodes as well as the EGM sensing and pacing electrodes described above is set forth in FIG. 21. It will be understood that the simplified block diagram does not show all of the conventional components and circuitry of such ICDs including digital clocks and clock lines, low voltage power supply and supply lines for powering the circuits and providing pacing pulses or telemetry circuits for telemetry transmissions between the ICD and an external programmer or monitor.

Figure 21:
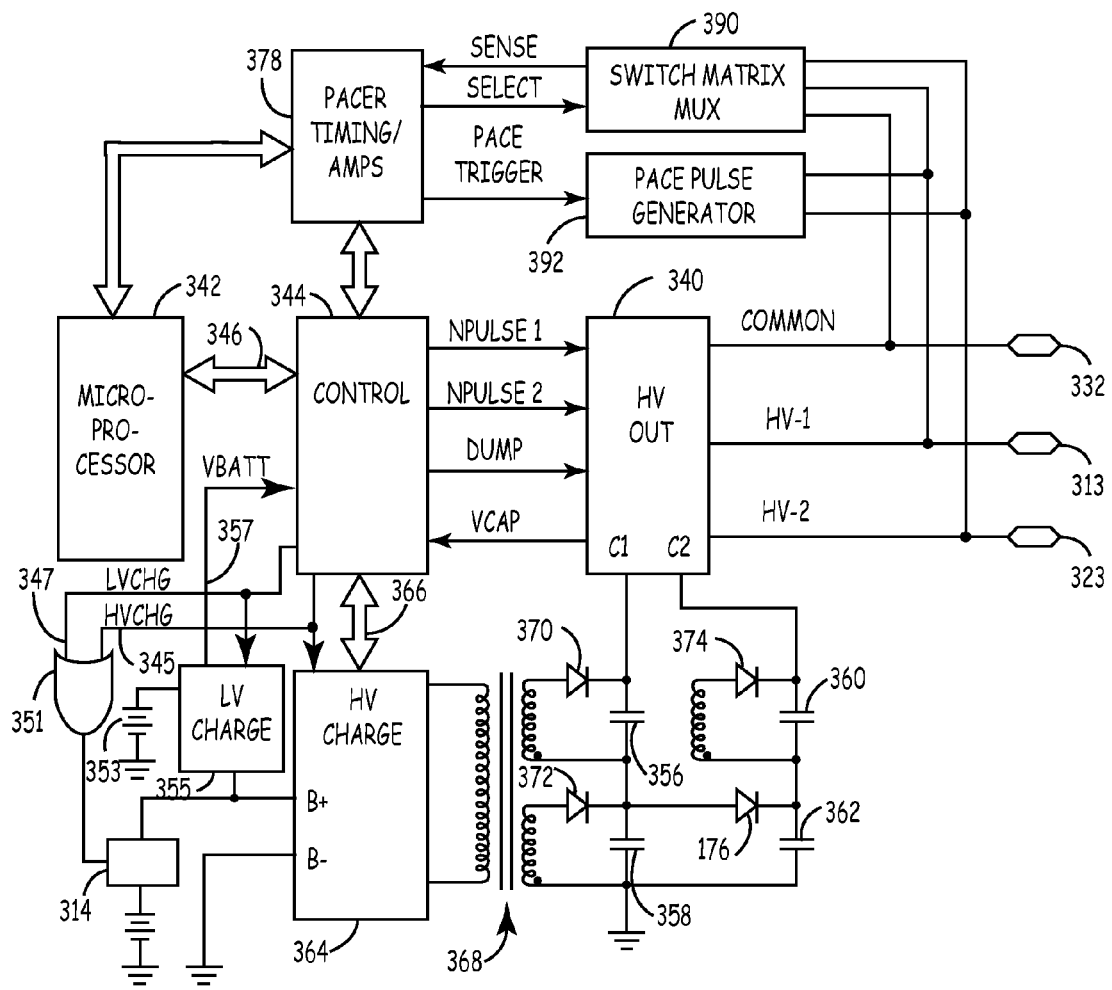
FIG. 21 illustrates a block diagram of the circuitry of the SubQ ICD of FIGS. 1-15.
Figure 22:
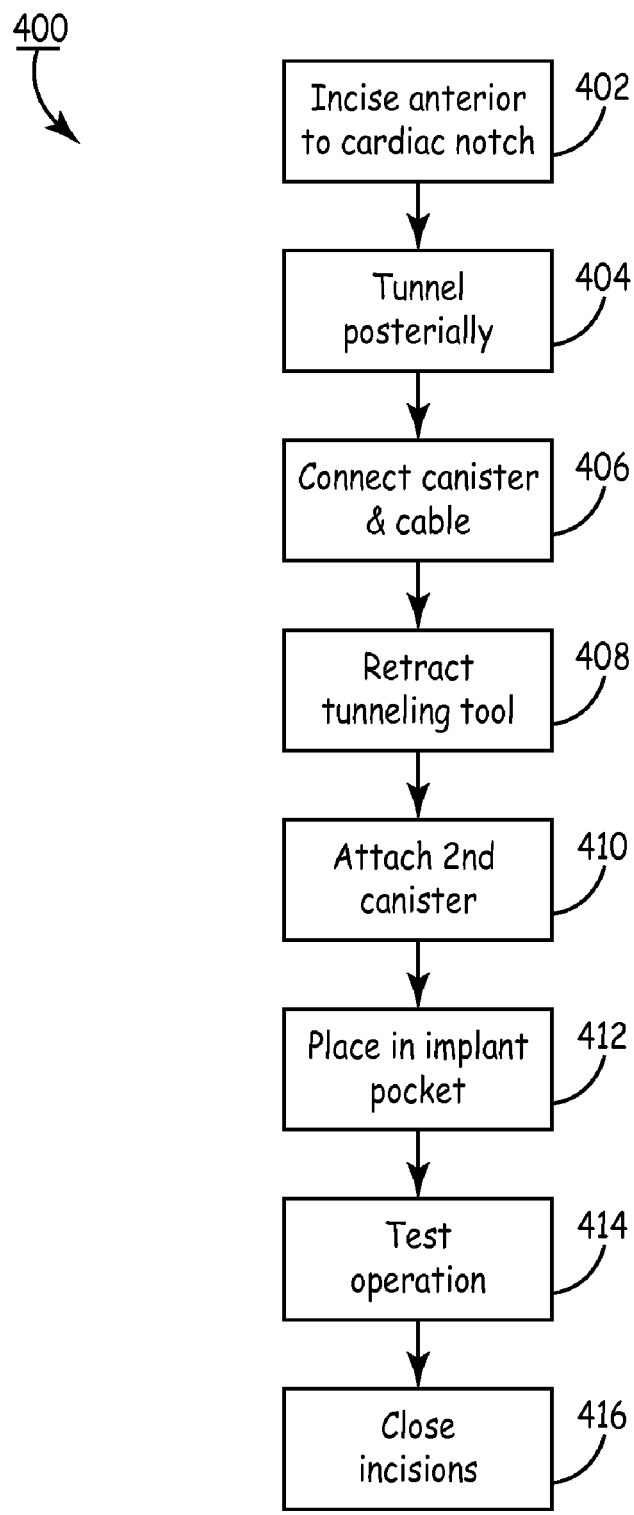
FIG. 22 illustrates an exemplary method of implant of the SubQ ICD depicted in FIGS. 4A and 5A.

FIG. 21 illustrates the electronic circuitry, low voltage and high voltage batteries within the hermetically sealed housings. The low voltage battery 353 is coupled to a power supply (not shown) that supplies power to the ICD circuitry and the pacing output capacitors to supply pacing energy in a manner well known in the art. The low voltage battery can comprise one or two conventional LiCF$_x$, LiMnO$_2$ or LiI$_2$ cells. The high voltage battery 312 can comprise one or two conventional LiSVO or LiMnO$_2$ cell.

In FIG. 21, SubQ ICD functions are controlled by means of stored software, firmware and hardware that cooperatively monitor the EGM, determine when a cardioversion-defibrillation shock or pacing is necessary, and deliver prescribed cardioversion-defibrillation and pacing therapies. The block diagram of FIG. 21 incorporates circuitry set forth in commonly assigned U.S. Pat. Nos. 5,163,427 "Apparatus for Delivering Single and Multiple Cardioversion and Defibrillation Pulses" to Keimel; 5,188,105 "Apparatus and Method for Treating a Tachyarrhythmia" to Keimel and 5,314,451 "Replaceable Battery for Implantable Medical Device" to Mulier for selectively delivering single phase, simultaneous biphasic and sequential biphasic cardioversion-defibrillation shocks typically employing an ICD IPG housing electrode coupled to the COMMON output 332 of high voltage output circuit 340 and one or two cardioversion-defibrillation electrodes disposed in a heart chamber or cardiac vessel coupled to the HVI and HV-2 outputs (313 and 323, respectively) of the high voltage output circuit 340. The circuitry of the subcutaneous SubQ ICD of the present invention can be made simpler by adoption of one such cardioversion-defibrillation shock waveform for delivery simply between the first and second cardioversion-defibrillation electrodes 313 and 323 coupled to the HV-1 and HV-2 outputs respectively. Or, the third cardioversion-defibrillation electrode 332 can be coupled to the COMMON output as depicted in FIG. 21 and the first and second cardioversion-defibrillation electrodes 313 and 323 can be electrically connected in to the HV-1 and the HV-2 outputs, respectively, as depicted in FIG. 21.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The ICD of the present invention uses maximum voltages in the range of about 700 to about 3150 Volts and is associated with energies of about 25 Joules to about 210 Joules. The total high voltage capacitance could range from about 50 to about 300 microfarads.

Such cardioversion-defibrillation shocks are only delivered when a malignant tachyarrhythmia, e.g., ventricular fibrillation is detected through processing of the far field cardiac EGM employing one of the available detection algorithms known in the ICD art.

In FIG. 21, pacer timing/sense amplifier circuit 378 processes the far field EGM SENSE signal that is developed across a particular EGM sense vector defined by a selected pair of the electrodes 332, 313 and, optionally, electrode 323 if present as noted above. The selection of the sensing electrode pair is made through the switch matrix/MUX 390 in a manner disclosed in the commonly assigned U.S. Pat. No. 5,331,966 "Subcutaneous Multi-Electrode Sensing System, Method and Pacer" to Bennett, et al patent to provide the most reliable sensing of the EGM signal of interest, which would be the R wave for patients who are believed to be at risk of ventricular fibrillation leading to sudden death. The far field EGM signals are passed through the switch matrix/MUX 390 to the input of a sense amplifier in the pacer timing/sense amplifier circuit 378. Bradycardia is typically determined by an escape interval timer within the pacer timing circuit 378 or the timing and control circuit 344, and pacing pulses that develop a PACE TRIGGER signal applied to the pacing pulse generator 392 when the interval between successive R-waves exceeds the escape interval. Bradycardia pacing is often temporarily provided to maintain cardiac output after delivery of a cardioversion-defibrillation shock that may cause the heart to slowly beat as it recovers function.

Detection of a malignant tachyarrhythmia is determined in the timing and control circuit 344 as a function of the intervals between R-wave sense event signals that are output from the pacer timing/sense amplifier circuit 378 to the timing and control circuit 344.

Certain steps in the performance of the detection algorithm criteria are cooperatively performed in a microcomputer 342, including microprocessor, RAM and ROM, associated circuitry, and stored detection criteria that may be programmed into RAM via a telemetry interface (not shown) conventional in the art. Data and commands are exchanged between microcomputer 342 and timing and control circuit 344, pacer timing/amplifier circuit 378, and high voltage output circuit 340 via a bidirectional data/control bus 346. The pacer timing/amplifier circuit 378 and the timing and control circuit 344 are clocked at a slow clock rate. The microcomputer 342 is normally asleep, but is awakened and operated by a fast clock by interrupts developed by each it-wave sense event or on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pace/sense circuitry 378. The algorithms and functions of the microcomputer 342 and timer and control circuit 344 employed and performed in detection of tachyarrhythmias are set forth, for example, in commonly assigned U.S. Pat. Nos. 5,991,656 "Prioritized Rule Based Apparatus for Diagnosis and Treatment of Arrhythmias" to Olson, et al and 5,193,535 "Method and Apparatus for Discrimination of Ventricular Tachycardia from Ventricular Fibrillation and for Treatment Thereof" to Bardy, et al, for example. Particular algorithms for detection of ventricular fibrillation and malignant ventricular tachycardias can be selected from among the comprehensive algorithms for distinguishing atrial and ventricular tachyarrhythmias from one another and from high rate sinus rhythms that are set forth in the '656 and '535 patents.

The detection algorithms are highly sensitive and specific for the presence or absence of life threatening ventricular arrhythmias, e.g., ventricular tachycardia (V-TACH) and ventricular fibrillation (V-FIB). Another optional aspect of the present invention is that the operational circuitry can detect the presence of atrial fibrillation (A FIB) as described in Olson, W. et al. "Onset And Stability For Ventricular Tachyarrhythmia Detection in an Implantable Cardioverter and Defibrillator," Computers in Cardiology (1986) pp. 167-170. Detection can be provided via R-R Cycle length instability detection algorithms. Once A-FIB has been detected, the operational circuitry will then provide QRS synchronized atrial cardioversion/defibrillation using the same shock energy and wave shapes used for ventricular cardioversion/defibrillation.

Operating modes and parameters of the detection algorithm are programmable and the algorithm is focused on the detection of V-FIB and high rate V-TACH (>240 bpm).

Although the SubQ ICD of the present invention may rarely be used for an actual sudden death event, the simplicity of design and implementation allows it to be employed in large populations of patients at modest risk with modest cost by medical personnel other than electrophysiologists. Consequently, the ICD of the present invention includes the automatic detection and therapy of the most malignant rhythm disorders. As part of the detection algorithm's applicability to children, the upper rate range is programmable upward for use in children, known to have rapid supraventricular tachycardias and more rapid V-FIB.

When a malignant tachycardia is detected, high voltage capacitors 356, 358, 360, and 362 are charged to a pre-programmed voltage level by a high-voltage charging circuit 364. It is generally considered inefficient to maintain a constant charge on the high voltage output capacitors 356, 358, 360, 362. Instead, charging is initiated when control circuit 344 issues a high voltage charge command HVCHG delivered on line 345 to high voltage charge circuit 364 and charging is controlled by means of bi-directional control/data bus 366 and a feedback signal VCAP from the HV output circuit 340. High voltage output capacitors 356, 358, 360 and 362 may be of film, aluminum electrolytic or wet tantalum construction.

The negative terminal of high voltage battery 312 is directly coupled to system ground. Switch circuit 314 is normally open so that the positive terminal of high voltage battery 312 is disconnected from the positive power input of the high voltage charge circuit 364. The high voltage charge command HVCHG is also conducted via conductor 349 to the control input of switch circuit 314, and switch circuit 314 closes in response to connect positive high voltage battery voltage EXT B+ to the positive power input of high voltage charge circuit 364. Switch circuit 314 may be, for example, a field effect transistor (FET) with its source-to-drain path interrupting the EXT B+ conductor 318 and its gate receiving the HVCHG signal on conductor 345. High voltage charge circuit 364 is thereby rendered ready to begin charging the high voltage output capacitors 356, 358, 360, and 362 with charging current from high voltage battery 312.

High voltage output capacitors 356, 358, 360, and 362 may be charged to very high voltages, e.g., 700-3150V, to be discharged through the body and heart between the selected electrode pairs among first, second, and, optionally, third subcutaneous cardioversion-defibrillation electrodes 313, 332, and 323. The details of the voltage charging circuitry are also not deemed to be critical with regard to practicing the present invention; one high voltage charging circuit believed to be suitable for the purposes of the present invention is disclosed. High voltage capacitors 356, 358, 360, and 362 are charged by high voltage charge circuit 364 and a high frequency, high-voltage transformer 368 as described in detail in commonly assigned U.S. Pat. No. 4,548,209 "Energy Converter for Implantable Cardioverter" to Wielders, et al. Proper charging polarities are maintained by diodes 370, 372, 374 and 376 interconnecting the output windings of high-voltage transformer 368 and the capacitors 356, 358, 360, and 362. As noted above, the state of capacitor charge is monitored by circuitry within the high voltage output circuit 340 that provides a VCAP, feedback signal indicative of the voltage to the timing and control circuit 344. Timing and control circuit 344 terminates the high voltage charge command HVCHG when the VCAP signal matches the programmed capacitor output voltage, i.e., the cardioversion-defibrillation peak shock voltage.

Timing and control circuit 344 then develops first and second control signals NPULSE 1 and NPULSE 2, respectively, that are applied to the high voltage output circuit 340 for triggering the delivery of cardioverting or defibrillating shocks. In particular, the NPULSE 1 signal triggers discharge of the first capacitor bank, comprising capacitors 356 and 358. The NPULSE 2 signal triggers discharge of the first capacitor bank and a second capacitor bank, comprising capacitors 360 and 362. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 344 serves to control operation of the high voltage output stage 340, which delivers high energy cardioversion-defibrillation shocks between a selected pair or pairs of the first, second, and, optionally, the third cardioversion-defibrillation electrodes 313, 323, and 332 coupled to the HV-1, HV-2 and optionally to the COMMON output as shown in FIG. 21.

Thus, SubQ ICD 10 monitors the patient's cardiac status and initiates the delivery of a cardioversion-defibrillation shock through a selected pair or pairs of the first, second and third cardioversion-defibrillation electrodes 313, 323 and 332 in response to detection of a tachyarrhythmia requiring cardioversion-defibrillation. The high HVCHG signal causes the high voltage battery 312 to be connected through the switch circuit 314 with the high voltage charge circuit 364 and the charging of output capacitors 356, 358, 360, and 362 to commence. Charging continues until the programmed charge voltage is reflected by the VCAP signal, at which point control and timing circuit 344 sets the HVCHG signal low terminating charging and opening switch circuit 314. Typically, the charging cycle takes only fifteen to twenty seconds, and occurs very infrequently. The ICD 10 can be programmed to attempt to deliver cardioversion shocks to; the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state. A patient receiving the ICD 10 on a prophylactic basis would be instructed to report each such episode to the attending physician for further evaluation of the patient's condition and assessment for the need for implantation of a more sophisticated and long-lived ICD.

It will be apparent from the foregoing that while particular embodiments of the invention have been illustrated and described, various modifications can be made without departing from the spirit and scope of the invention. Accordingly, it is not intended that the invention be limited, except as by the appended claims.

What is claimed is:

1. A housing for a subcutaneous cardioverter defibrillator for delivering stimulation therapy to a heart, comprising:
   a housing structure comprising:
      a first surface and a second surface, said first surface being continuous, smooth, unitary and spaced from said second surface and extending from a housing proximal end to a housing distal end;
      a contour of said first surface being alterable in order to be non-linear; and
      a perimeter of said housing structure forming a curvilinear edge;
   a first electrode positioned on the first surface proximate the housing proximal end; and
   a second electrode positioned on the first surface proximate the housing distal end;
   wherein the housing structure has a first position and a second position, the first position corresponding to the first surface and the second surface being substantially planar, and the second position corresponding to the second surface forming a convex surface and the first surface forming a concave surface opposing the second surface so that the first electrode is laterally located in opposition to the second electrode.

2. The housing of claim 1 wherein the first electrode includes an active-electrode.

3. The housing of claim 1 wherein said housing is adapted to be deployed in a subcutaneous location in a patient, said subcutaneous location including a left anterior portion of a patient's thorax between a third rib and a sixth rib of the patient.

4. The housing of claim 3 wherein said subcutaneous location includes one of a location adjacent a portion of latissimus dorsi muscle of the patient; a location adjacent a portion of an external abdominal oblique muscle of the patient; and a location adjacent an overlaying portion of a sternum of the patient.

5. The housing of claim 1 wherein said subcutaneous location includes one of a location in proximity of a major muscle of the patient; a location on the major muscle of the patient; a location associated with a portion of an infranginous muscle of the patient; a location adjacent a portion of a teres minus muscle of the patient; and a portion adjacent the cardiac notch of the patient.

6. The housing of claim 1 with the second surface being formed with a plurality of segments allowing the first surface and the second surface to dynamically form the concave surface and the convex surface, respectively.

7. The housing of claim 6 with the first surface being continuous.

8. A cardioversion defibrillation device, comprising:
a housing structure, comprising:
  a first surface and a second surface, said first surface being continuous, smooth, unitary and integrally formed and spaced from said second surface and extending from a housing proximal end to a housing distal end;
  a contour of said first surface being alterable in order to be non-linear; and
  a perimeter of said housing structure forming a curvilinear edge;
a first electrode positioned on the first surface proximate the housing proximal end; and
a second electrode positioned on the second surface proximate the housing proximal end; and
a cardioversion defibrillation circuit contained within the housing structure and coupled to the first electrode and the second electrode;
wherein the housing structure has a first position and a second position, the first position corresponding to the first surface and the second surface being substantially planar, and the second position corresponding to the second surface forming a convex surface and the first surface forming a concave surface opposing the second surface so that the first electrode is laterally located in opposition to the second electrode.

9. The cardioversion defibrillation device of claim 8 further comprising a lead connector port positioned on the housing structure to couple the cardioversion defibrillation circuit to a distal electrode positioned on a lead.

10. The cardioversion defibrillation device of claim 8 wherein the first electrode includes an active electrode.

11. The cardioversion defibrillation device of claim 8 wherein the housing is adapted to be deployed in a subcutaneous location in a patient, the subcutaneous location including a left anterior portion of a patient's thorax between a third rib and a sixth rib of the patient.

12. The cardioversion defibrillation device of claim 11 wherein the subcutaneous location includes one of a location adjacent a portion of a latissimus dorsi muscle of the patient; a location adjacent a portion of an external abdominal oblique muscle of the patient; and a location adjacent an overlaying portion of a sternum of the patient.

13. The cardioversion defibrillation device of claim 8 wherein the subcutaneous location includes one of a location in proximity of a major muscle of the patient; a location on the major muscle of the patient; a location associated with a portion of an infranginous muscle of the patient; a location adjacent a portion of a teres minus muscle of the patient; and a portion adjacent to a cardiac notch of the patient.

14. The cardioversion defibrillation device of claim 8 with the second surface being formed with a plurality of segments allowing the first surface and the second surface to dynamically form the concave surface and the convex surface, respectively.

15. The cardioversion defibrillation device of claim 14 with the first surface being continuous.

* * * * *